US012369857B2

(12) United States Patent
Feldshon et al.

(10) Patent No.: US 12,369,857 B2
(45) Date of Patent: Jul. 29, 2025

(54) INFECTION RISK DETECTION USING EAR-WEARABLE SENSOR DEVICES

(71) Applicant: Starkey Laboratories, Inc., Eden Prairie, MN (US)

(72) Inventors: Archelle Georgiou Feldshon, Wayzata, MN (US); Krishna Chaithanya Vastare, Eden Prairie, MN (US); Justin R. Burwinkel, Eden Prairie, MN (US); Andy S. Lin, Chanhassen, MN (US); Kyle Olson, St. Louis Park, MN (US); Michael Karl Sacha, Chanhassen, MN (US); Amit Shahar, Hod HaSharon (IL)

(73) Assignee: Starkey Laboratories, Inc., Eden Prairie, MN (US)

( * ) Notice: Subject to any disclaimer, the term of this patent is extended or adjusted under 35 U.S.C. 154(b) by 455 days.

(21) Appl. No.: 17/834,569

(22) Filed: Jun. 7, 2022

(65) Prior Publication Data

US 2022/0386959 A1 Dec. 8, 2022

Related U.S. Application Data

(60) Provisional application No. 63/197,849, filed on Jun. 7, 2021.

(51) Int. Cl.

| | |
|---|---|
| ***A61B 5/00*** | (2006.01) |
| ***G16H 10/60*** | (2018.01) |

(52) U.S. Cl.

CPC .......... *A61B 5/6817* (2013.01); *A61B 5/0004* (2013.01); *A61B 5/0024* (2013.01);

(Continued)

(58) Field of Classification Search

CPC ... A61B 5/6817; A61B 5/0004; A61B 5/0024; A61B 5/7225; A61B 5/7275;

(Continued)

(56) References Cited

U.S. PATENT DOCUMENTS

| | | | |
|---|---|---|---|
| 6,821,249 B2 | 11/2004 | Casscells et al. | |
| 9,167,356 B2 | 10/2015 | Higgins et al. | |

(Continued)

FOREIGN PATENT DOCUMENTS

| | | | |
|---|---|---|---|
| EP | 2400884 | 1/2012 | |
| EP | 2400884 B1 * | 3/2018 | .............. A61B 5/00 |

(Continued)

OTHER PUBLICATIONS

Dabrowska et al, The immune response to surgery and infection. Central European Journal of Immunology. vol. 39(4) 2014, p. 532-537 [online], [retrieved on Sep. 29, 2024]. Retreived from the Internet <URL: https://www.ncbi.nlm.nih.gov/pmc/articles/PMC4439968/pdf/CEJI-39-47741.pdf> (Year: 2014).*

(Continued)

*Primary Examiner* — Gary Jackson
*Assistant Examiner* — Sebastian X Lukjan
(74) *Attorney, Agent, or Firm* — Pauly, DeVries Smith & Deffner LLC

(57) ABSTRACT

Embodiments herein relate to ear-wearable devices and systems that can detect a risk of infection in a device wearer. In a first aspect, an ear-wearable infection sensor device is included having a control circuit, a microphone, a sensor package, and an electroacoustic transducer, wherein the electroacoustic transducer is in electrical communication with the control circuit. The ear-wearable infection sensor device can be configured to analyze data from the sensor package to determine physiological parameters of a device wearer and evaluate the physiological parameters to detect (Continued)

the risk of an infection. Other embodiments are also included herein.

20 Claims, 13 Drawing Sheets

(52) U.S. Cl.
CPC .......... *A61B 5/7225* (2013.01); *A61B 5/7275* (2013.01); *A61B 5/7285* (2013.01); *G16H 10/60* (2018.01)

(58) Field of Classification Search
CPC ....... A61B 5/7285; A61B 5/01; A61B 5/1118; A61B 5/20; A61B 5/4205; A61B 5/4833; A61B 5/6815; A61B 5/0022; G16H 10/60
See application file for complete search history.

(56) References Cited

U.S. PATENT DOCUMENTS

| | | | | |
|---|---|---|---|---|
| 9,848,273 | B1 | 12/2017 | Helwani et al. | |
| 9,924,879 | B2 | 3/2018 | Van Den Heuvel et al. | |
| 11,646,098 | B1 * | 5/2023 | McNair | G16H 50/30<br>702/19 |
| 2019/0006031 | A1 * | 1/2019 | Hyde | G16H 40/20 |
| 2019/0117155 | A1 | 4/2019 | Cross et al. | |
| 2020/0121189 | A1 * | 4/2020 | Farr | A61B 1/00009 |
| 2022/0005601 | A1 * | 1/2022 | Cox | A61B 5/742 |

FOREIGN PATENT DOCUMENTS

| | | | | |
|---|---|---|---|---|
| WO | 2020264203 | | 12/2020 | |
| WO | WO-2021046237 | A1 * | 3/2021 | A61B 5/0077 |
| WO | WO-2021212112 | A1 * | 10/2021 | A61B 5/0205 |
| WO | WO-2021234037 | A1 * | 11/2021 | A61B 5/0022 |
| WO | WO-2022167065 | A1 * | 8/2022 | A61B 5/0022 |
| WO | 2022261107 | | 12/2022 | |

OTHER PUBLICATIONS

Lonini, Luca, et al. "Rapid Screening of Physiological Changes Associated with COVID-19 using Soft-Wearables and Structured Activities: A Pilot Study," IEEEJournal of Transactional Engineering in Health and Medicine, vol. 9, 2021 (11 pages).

"International Search Report and Written Opinion," for PCT Application No. PCT/US2022/032517 mailed Oct. 21, 2022 (15 pages).

"International Preliminary Report on Patentability," for PCT Application No. PCT/US2022/032517 mailed Dec. 21, 2023 (10 pages).

* cited by examiner

INFECTION RISK DETECTION USING EAR-WEARABLE SENSOR DEVICES

This application claims the benefit of U.S. Provisional Application No. 63/197,849 filed Jun. 7, 2021, the content of which is herein incorporated by reference in its entirety.

FIELD

Embodiments herein relate to ear-wearable devices and systems that can detect a risk of infection in a device wearer.

BACKGROUND

Infections represent a substantial threat to human health. Infections can include viral infections, bacterial infections, fungal infections, and the like. Infections can occur because of a weakened immune system, secondary to a medical or surgical procedure, after ingesting contaminated food or water, after exposure to another individual who is infected, or through various other scenarios. Infections can cause substantial direct harm as well as indirect harm such as through their impact on inflammation.

In many cases, an individual's immune system functions to stop infections before they become a substantial threat to overall health. However, sometimes infections require medical intervention to be properly resolved. Where required, early medical intervention can be critical to achieving the best health outcomes.

SUMMARY

Embodiments herein relate to ear-wearable devices and systems that can detect a risk of infection in a device wearer.
In a first aspect, an ear-wearable infection sensor device is included having a control circuit, a microphone, wherein the microphone is in electrical communication with the control circuit, a sensor package, wherein the sensor package is in electrical communication with the control circuit, and an electroacoustic transducer, wherein the electroacoustic transducer is in electrical communication with the control circuit. The ear-wearable infection sensor device can be configured to analyze data from the sensor package to determine physiological parameters of a device wearer and evaluate the physiological parameters to detect the risk of an infection.

In a second aspect, in addition to one or more of the preceding or following aspects, or in the alternative to some aspects, the sensor package can include a photoplethysmography (PPG) sensor.

In a third aspect, in addition to one or more of the preceding or following aspects, or in the alternative to some aspects, the physiological parameters can include at least one of a respiration rate, a heart rate, and SpO2.

In a fourth aspect, in addition to one or more of the preceding or following aspects, or in the alternative to some aspects, the physiological parameters can include a temperature.

In a fifth aspect, in addition to one or more of the preceding or following aspects, or in the alternative to some aspects, the ear-wearable infection sensor device is configured to evaluate a duration of a temperature elevation.

In a sixth aspect, in addition to one or more of the preceding or following aspects, or in the alternative to some aspects, the ear-wearable infection sensor device is configured to evaluate a time course of a temperature elevation.

In a seventh aspect, in addition to one or more of the preceding or following aspects, or in the alternative to some aspects, the temperature reflects a real-time temperature, a short-term temperature, a long-term temperature, or a circadian temperature.

In an eighth aspect, in addition to one or more of the preceding or following aspects, or in the alternative to some aspects, the sensor package can include a temperature sensor, wherein the temperature sensor is configured for placement within the ear canal.

In a ninth aspect, in addition to one or more of the preceding or following aspects, or in the alternative to some aspects, the ear-wearable infection sensor device is configured to evaluate a sequence of changes in the physiological parameters as part of evaluating the physiological parameters.

In a tenth aspect, in addition to one or more of the preceding or following aspects, or in the alternative to some aspects, the ear-wearable infection sensor device is configured to analyze data from the microphone to evaluate breathing sounds of the device wearer in combination with evaluating the physiological parameters to detect the risk of the infection.

In an eleventh aspect, in addition to one or more of the preceding or following aspects, or in the alternative to some aspects, the sensor package can include a motion sensor, wherein the ear-wearable infection sensor device is configured to evaluate physical activity of the device wearer using signals from the motion sensor in combination with evaluating the physiological parameters to detect the risk of the infection.

In a twelfth aspect, in addition to one or more of the preceding or following aspects, or in the alternative to some aspects, the infection can include a bacterial infection.

In a thirteenth aspect, in addition to one or more of the preceding or following aspects, or in the alternative to some aspects, the infection can include a viral infection.

In a fourteenth aspect, in addition to one or more of the preceding or following aspects, or in the alternative to some aspects, the infection can include a parasitic infection.

In a fifteenth aspect, in addition to one or more of the preceding or following aspects, or in the alternative to some aspects, the infection can include at least one of a fungal, protozoal, helminthic, and prion infection.

In a sixteenth aspect, in addition to one or more of the preceding or following aspects, or in the alternative to some aspects, the sensor package can include a pressure sensor and a motion sensor, wherein the ear-wearable infection sensor device is configured to detect orthostatic hypotension using data from the pressure sensor and the motion sensor.

In a seventeenth aspect, in addition to one or more of the preceding or following aspects, or in the alternative to some aspects, the pressure sensor can include at least one selected from the group consisting of a piezoelectric sensor and a graphene sensor.

In an eighteenth aspect, in addition to one or more of the preceding or following aspects, or in the alternative to some aspects, the ear-wearable infection sensor device is configured to evaluate the physiological parameters while the device wearer is in a resting state.

In a nineteenth aspect, in addition to one or more of the preceding or following aspects, or in the alternative to some aspects, the ear-wearable infection sensor device is configured to compare the physiological parameters reflecting the device wearer in a resting state versus the device wearer in a non-resting state.

In a twentieth aspect, in addition to one or more of the preceding or following aspects, or in the alternative to some aspects, the ear-wearable infection sensor device is configured to gather baseline data over a first time period.

In a twenty-first aspect, in addition to one or more of the preceding or following aspects, or in the alternative to some aspects, the baseline data is gathered after a period of detected physical activity falling below a threshold value.

In a twenty-second aspect, in addition to one or more of the preceding or following aspects, or in the alternative to some aspects, the baseline data can include baseline temperature data.

In a twenty-third aspect, in addition to one or more of the preceding or following aspects, or in the alternative to some aspects, the ear-wearable infection sensor device is configured to characterize a baseline pattern based on the gathered baseline data.

In a twenty-fourth aspect, in addition to one or more of the preceding or following aspects, or in the alternative to some aspects, the ear-wearable infection sensor device is configured to compare the baseline data with real time data during a second time period.

In a twenty-fifth aspect, in addition to one or more of the preceding or following aspects, or in the alternative to some aspects, the comparison is performed with the data normalized for circadian effects.

In a twenty-sixth aspect, in addition to one or more of the preceding or following aspects, or in the alternative to some aspects, the ear-wearable infection sensor device is configured to identify a sub-fever level temperature elevation.

In a twenty-seventh aspect, in addition to one or more of the preceding or following aspects, or in the alternative to some aspects, the ear-wearable infection sensor device is configured to identify a fever level temperature elevation.

In a twenty-eighth aspect, in addition to one or more of the preceding or following aspects, or in the alternative to some aspects, the ear-wearable infection sensor device is configured to normalize the physiological parameters for estimated fatigue and stress.

In a twenty-ninth aspect, in addition to one or more of the preceding or following aspects, or in the alternative to some aspects, the ear-wearable infection sensor device is configured to normalize the physiological parameters for at least one of estimated anxiety and mental status.

In a thirtieth aspect, in addition to one or more of the preceding or following aspects, or in the alternative to some aspects, the ear-wearable infection sensor device is configured to estimate at least one of pain and discomfort experienced by the device wearer based on data from at least one of the microphone and the sensor package.

In a thirty-first aspect, in addition to one or more of the preceding or following aspects, or in the alternative to some aspects, the ear-wearable infection sensor device is configured to evaluate breathing sounds.

In a thirty-second aspect, in addition to one or more of the preceding or following aspects, or in the alternative to some aspects, the ear-wearable infection sensor device to evaluate breathing sounds at discrete points of a respiration cycle.

In a thirty-third aspect, in addition to one or more of the preceding or following aspects, or in the alternative to some aspects, the ear-wearable infection sensor device to evaluate left-side versus right-side breathing sounds.

In a thirty-fourth aspect, in addition to one or more of the preceding or following aspects, or in the alternative to some aspects, the ear-wearable infection sensor device is configured to identify a cough.

In a thirty-fifth aspect, in addition to one or more of the preceding or following aspects, or in the alternative to some aspects, the ear-wearable infection sensor device is configured to distinguish between a wet cough and a dry cough.

In a thirty-sixth aspect, in addition to one or more of the preceding or following aspects, or in the alternative to some aspects, the ear-wearable infection sensor device is configured to identify a sneeze.

In a thirty-seventh aspect, in addition to one or more of the preceding or following aspects, or in the alternative to some aspects, the ear-wearable infection sensor device is configured to receive and utilize seasonal infection trend data.

In a thirty-eighth aspect, in addition to one or more of the preceding or following aspects, or in the alternative to some aspects, the ear-wearable infection sensor device is configured to receive and utilize geographic infection trend data.

In a thirty-ninth aspect, in addition to one or more of the preceding or following aspects, or in the alternative to some aspects, the ear-wearable infection sensor device is configured to receive information regarding previous infections of a device wearer.

In a fortieth aspect, in addition to one or more of the preceding or following aspects, or in the alternative to some aspects, the ear-wearable infection sensor device is configured to receive information from a secondary device regarding sputum.

In a forty-first aspect, in addition to one or more of the preceding or following aspects, or in the alternative to some aspects, the ear-wearable infection sensor device is configured to generate a sound and record received reflected sound.

In a forty-second aspect, in addition to one or more of the preceding or following aspects, or in the alternative to some aspects, the sensor package can include an optical color sensor.

In a forty-third aspect, in addition to one or more of the preceding or following aspects, or in the alternative to some aspects, the ear-wearable infection sensor device is configured to evaluate a real-time skin color compared with a baseline skin color for the device wearer.

In a forty-fourth aspect, in addition to one or more of the preceding or following aspects, or in the alternative to some aspects, the ear-wearable infection sensor device is configured to analyze data from the sensor package to determine a posture of the device wearer.

In a forty-fifth aspect, in addition to one or more of the preceding or following aspects, or in the alternative to some aspects, the ear-wearable infection sensor device is configured to classify a set of data from at least one of the sensor package and the microphone into a category from amongst a set of categories.

In a forty-sixth aspect, in addition to one or more of the preceding or following aspects, or in the alternative to some aspects, the category reflects a probability of an infection.

In a forty-seventh aspect, in addition to one or more of the preceding or following aspects, or in the alternative to some aspects, the category reflects a severity of an infection.

In a forty-eighth aspect, in addition to one or more of the preceding or following aspects, or in the alternative to some aspects, the category reflects a type of an infection.

In a forty-ninth aspect, in addition to one or more of the preceding or following aspects, or in the alternative to some aspects, the ear-wearable infection sensor device is configured to match a set of data from at least one of the sensor package and the microphone against a plurality of predetermined patterns to determine infection status.

In a fiftieth aspect, in addition to one or more of the preceding or following aspects, or in the alternative to some aspects, the ear-wearable infection sensor device is configured to match changes in data from at least one of the sensor package and the microphone against a plurality of predetermined patterns of changes in data to determine infection status.

In a fifty-first aspect, in addition to one or more of the preceding or following aspects, or in the alternative to some aspects, the ear-wearable infection sensor device is configured to query the device wearer regarding how they feel.

In a fifty-second aspect, in addition to one or more of the preceding or following aspects, or in the alternative to some aspects, the ear-wearable infection sensor device is configured to issue an alert if a risk of infection is detected.

In a fifty-third aspect, in addition to one or more of the preceding or following aspects, or in the alternative to some aspects, the ear-wearable infection sensor device is configured to instruct the device wearer to look at an accessory device with a camera if a risk of infection is detected.

In a fifty-fourth aspect, in addition to one or more of the preceding or following aspects, or in the alternative to some aspects, the ear-wearable infection sensor device is configured to instruct the device wearer to hold an accessory device against their chest if a risk of infection is detected.

In a fifty-fifth aspect, in addition to one or more of the preceding or following aspects, or in the alternative to some aspects, the ear-wearable infection sensor device is configured to change a threshold for detecting the risk of an infection based on data regarding one or more of the device wearer health history, age, gender, weight, medication status, and BMI.

In a fifty-sixth aspect, in addition to one or more of the preceding or following aspects, or in the alternative to some aspects, the ear-wearable infection sensor device is configured to change a threshold for detecting the risk of an infection based on data regarding previous infections experienced by the device wearer.

In a fifty-seventh aspect, in addition to one or more of the preceding or following aspects, or in the alternative to some aspects, the ear-wearable infection sensor device is configured to change a threshold for detecting the risk of an infection based on data regarding previous surgical procedures experienced by the device wearer.

In a fifty-eighth aspect, in addition to one or more of the preceding or following aspects, or in the alternative to some aspects, the ear-wearable infection sensor device is configured to change a threshold for detecting the risk of an infection based on geolocation data reflecting past locations of the device wearer.

In a fifty-ninth aspect, in addition to one or more of the preceding or following aspects, or in the alternative to some aspects, the ear-wearable infection sensor device is configured to change a threshold for detecting the risk of an infection based on an input from a care provider or a clinician.

In a sixtieth aspect, in addition to one or more of the preceding or following aspects, or in the alternative to some aspects, the ear-wearable infection sensor device is configured to use data regarding an activity level of the device wearer along with data regarding the physiological parameters to detect the risk of an infection.

In a sixty-first aspect, in addition to one or more of the preceding or following aspects, or in the alternative to some aspects, the ear-wearable infection sensor device is configured to use geolocation data to characterize an activity level of the device wearer.

In a sixty-second aspect, in addition to one or more of the preceding or following aspects, or in the alternative to some aspects, the ear-wearable infection sensor device is configured to use motion sensor data to characterize an activity level of the device wearer.

In a sixty-third aspect, in addition to one or more of the preceding or following aspects, or in the alternative to some aspects, the ear-wearable infection sensor device is configured to use microphone data to characterize an activity level of the device wearer.

In a sixty-fourth aspect, in addition to one or more of the preceding or following aspects, or in the alternative to some aspects, the ear-wearable infection sensor device is configured to receive data regarding physiological parameters from a separate wearable device.

In a sixty-fifth aspect, in addition to one or more of the preceding or following aspects, or in the alternative to some aspects, the ear-wearable infection sensor device is configured to receive data regarding the device wearer from a medical record system.

In a sixty-sixth aspect, in addition to one or more of the preceding or following aspects, or in the alternative to some aspects, the ear-wearable infection sensor device is configured to evaluate changes in physical activity using data from the sensor package along with the physiological parameters to detect the risk of an infection.

In a sixty-seventh aspect, in addition to one or more of the preceding or following aspects, or in the alternative to some aspects, the ear-wearable infection sensor device is configured to evaluate urination frequency using data from the sensor package along with the physiological parameters to detect the risk of an infection.

In a sixty-eighth aspect, in addition to one or more of the preceding or following aspects, or in the alternative to some aspects, the ear-wearable infection sensor device is a hearing assistance device.

In a sixty-ninth aspect, in addition to one or more of the preceding or following aspects, or in the alternative to some aspects, the ear-wearable infection sensor device is configured to exchange data with a second ear-wearable infection sensor device.

In a seventieth aspect, an ear-wearable infection sensor system is included having a first ear-wearable device and a second ear-wearable device. The first ear-wearable device can include a first control circuit, a first microphone, wherein a microphone is in electrical communication with a control circuit, a first electroacoustic transducer, wherein an electroacoustic transducer is in electrical communication with the control circuit, and a first sensor package, wherein a sensor package is in electrical communication with the control circuit. The second ear-wearable device can include a second control circuit, a second microphone, wherein the second microphone is in electrical communication with the second control circuit, a second electroacoustic transducer, wherein the second electroacoustic transducer is in electrical communication with the second control circuit, and a second sensor package, wherein the second sensor package is in electrical communication with the second control circuit. The ear-wearable infection sensor system can be configured to analyze data from the first and/or second sensor package to determine physiological parameters of a device wearer, and evaluate the physiological parameters to detect the risk of an infection.

In a seventy-first aspect, a method of detecting an infection using an ear-wearable device is included. The method can include analyzing data from a sensor package of the ear-wearable device to determine physiological parameters of a device wearer and evaluating the physiological parameters to detect a risk of an infection.

In a seventy-second aspect, in addition to one or more of the preceding or following aspects, or in the alternative to some aspects, the physiological parameters can include at least one of a respiration rate, a heart rate, and SpO2.

In a seventy-third aspect, in addition to one or more of the preceding or following aspects, or in the alternative to some aspects, the physiological parameters can include a temperature.

In a seventy-fourth aspect, in addition to one or more of the preceding or following aspects, or in the alternative to some aspects, the method can further include evaluating a duration of a temperature elevation.

In a seventy-fifth aspect, in addition to one or more of the preceding or following aspects, or in the alternative to some aspects, the method can further include evaluating a time course of a temperature elevation.

In a seventy-sixth aspect, in addition to one or more of the preceding or following aspects, or in the alternative to some aspects, the method can further include evaluating a sequence of changes in the physiological parameters as part of evaluating the physiological parameters.

In a seventy-seventh aspect, in addition to one or more of the preceding or following aspects, or in the alternative to some aspects, the method can further include analyzing data from the microphone to evaluate breathing sounds of the device wearer in combination with evaluating the physiological parameters to detect the risk of the infection.

In a seventy-eighth aspect, in addition to one or more of the preceding or following aspects, or in the alternative to some aspects, the method can further include evaluating physical activity of the device wearer using signals from the motion sensor in combination with evaluating the physiological parameters to detect the risk of the infection.

In a seventy-ninth aspect, in addition to one or more of the preceding or following aspects, or in the alternative to some aspects, the method can further include detecting orthostatic hypotension using data from a pressure sensor and a motion sensor.

In an eightieth aspect, in addition to one or more of the preceding or following aspects, or in the alternative to some aspects, the method can further include evaluating the physiological parameters while the device wearer is in a resting state.

In an eighty-first aspect, in addition to one or more of the preceding or following aspects, or in the alternative to some aspects, the method can further include comparing the physiological parameters reflecting the device wearer in a resting state versus the device wearer in a non-resting state.

In an eighty-second aspect, in addition to one or more of the preceding or following aspects, or in the alternative to some aspects, the method can further include gathering baseline data over a first time period.

In an eighty-third aspect, in addition to one or more of the preceding or following aspects, or in the alternative to some aspects, wherein gathering baseline data over a first time period further includes characterizing a baseline pattern based on the gathered baseline data.

In an eighty-fourth aspect, in addition to one or more of the preceding or following aspects, or in the alternative to some aspects, the method can further include comparing the baseline data with real time data during a second time period.

In an eighty-fifth aspect, in addition to one or more of the preceding or following aspects, or in the alternative to some aspects, the method can further include normalizing the real time data based on circadian effects.

In an eighty-sixth aspect, in addition to one or more of the preceding or following aspects, or in the alternative to some aspects, the method can further include gathering baseline data after a period of detected physical activity falling below a threshold value.

In an eighty-seventh aspect, in addition to one or more of the preceding or following aspects, or in the alternative to some aspects, the method can further include identifying a sub-fever level temperature elevation.

In an eighty-eighth aspect, in addition to one or more of the preceding or following aspects, or in the alternative to some aspects, the method can further include identifying a fever level temperature elevation.

In an eighty-ninth aspect, in addition to one or more of the preceding or following aspects, or in the alternative to some aspects, the method can further include normalizing the physiological parameters for estimated fatigue and stress.

In a ninetieth aspect, in addition to one or more of the preceding or following aspects, or in the alternative to some aspects, the method can further include normalizing the physiological parameters for at least one of estimated anxiety and mental status.

In a ninety-first aspect, in addition to one or more of the preceding or following aspects, or in the alternative to some aspects, the method can further include estimating at least one of pain and discomfort experienced by the device wearer based on data from at least one of the microphone and the sensor package.

In a ninety-second aspect, in addition to one or more of the preceding or following aspects, or in the alternative to some aspects, the method can further include evaluating breathing sounds.

In a ninety-third aspect, in addition to one or more of the preceding or following aspects, or in the alternative to some aspects, the method can further include identifying a cough.

In a ninety-fourth aspect, in addition to one or more of the preceding or following aspects, or in the alternative to some aspects, the method can further include distinguishing between a wet cough and a dry cough.

In a ninety-fifth aspect, in addition to one or more of the preceding or following aspects, or in the alternative to some aspects, the method can further include evaluating breathing sounds at discrete points of a respiration cycle.

In a ninety-sixth aspect, in addition to one or more of the preceding or following aspects, or in the alternative to some aspects, the method can further include evaluating left-side versus right-side breathing sounds.

In a ninety-seventh aspect, in addition to one or more of the preceding or following aspects, or in the alternative to some aspects, the method can further include identifying a sneeze.

In a ninety-eighth aspect, in addition to one or more of the preceding or following aspects, or in the alternative to some aspects, the method can further include receiving and utilizing seasonal infection trend data.

In a ninety-ninth aspect, in addition to one or more of the preceding or following aspects, or in the alternative to some aspects, the method can further include receiving and utilizing geographic infection trend data.

In a one hundred and aspect, in addition to one or more of the preceding or following aspects, or in the alternative to some aspects, the method can further include receiving information regarding previous infections of a device wearer.

In a one hundred and first aspect, in addition to one or more of the preceding or following aspects, or in the alternative to some aspects, the method can further include receiving information from a secondary device regarding sputum.

In a one hundred and second aspect, in addition to one or more of the preceding or following aspects, or in the alternative to some aspects, the method can further include generating a sound and recording received reflected sound.

In a one hundred and third aspect, in addition to one or more of the preceding or following aspects, or in the alternative to some aspects, the method can further include evaluating a real-time skin color compared with a baseline skin color for the device wearer.

In a one hundred and fourth aspect, in addition to one or more of the preceding or following aspects, or in the alternative to some aspects, the method can further include analyzing data from the sensor package to determine a posture of the device wearer.

In a one hundred and fifth aspect, in addition to one or more of the preceding or following aspects, or in the alternative to some aspects, the method can further include classifying a set of data from at least one of the sensor package and the microphone into a category from amongst a set of categories.

In a one hundred and sixth aspect, in addition to one or more of the preceding or following aspects, or in the alternative to some aspects, the method can further include matching a set of data from at least one of the sensor package and the microphone against a plurality of predetermined patterns to determine infection status.

In a one hundred and seventh aspect, in addition to one or more of the preceding or following aspects, or in the alternative to some aspects, the method can further include matching changes in data from at least one of the sensor package and the microphone against a plurality of predetermined patterns of changes in data to determine infection status.

In a one hundred and eighth aspect, in addition to one or more of the preceding or following aspects, or in the alternative to some aspects, the method can further include querying the device wearer regarding how they feel.

In a one hundred and ninth aspect, in addition to one or more of the preceding or following aspects, or in the alternative to some aspects, the method can further include issuing an alert if a risk of infection is detected.

In a one hundred and tenth aspect, in addition to one or more of the preceding or following aspects, or in the alternative to some aspects, the method can further include instructing the device wearer to look at an accessory device with a camera if a risk of infection is detected.

In a one hundred and eleventh aspect, in addition to one or more of the preceding or following aspects, or in the alternative to some aspects, the method can further include instructing the device wearer to hold an accessory device against their chest if a risk of infection is detected.

In a one hundred and twelfth aspect, in addition to one or more of the preceding or following aspects, or in the alternative to some aspects, the method can further include changing a threshold for detecting the risk of an infection based on data regarding one or more of the device wearer health history, age, gender, weight, medication status, and BMI.

In a one hundred and thirteenth aspect, in addition to one or more of the preceding or following aspects, or in the alternative to some aspects, the method can further include changing a threshold for detecting the risk of an infection based on data regarding previous infections experienced by the device wearer.

In a one hundred and fourteenth aspect, in addition to one or more of the preceding or following aspects, or in the alternative to some aspects, the method can further include changing a threshold for detecting the risk of an infection based on data regarding previous surgical procedures experienced by the device wearer.

In a one hundred and fifteenth aspect, in addition to one or more of the preceding or following aspects, or in the alternative to some aspects, the method can further include changing a threshold for detecting the risk of an infection based on geolocation data reflecting past locations of the device wearer.

In a one hundred and sixteenth aspect, in addition to one or more of the preceding or following aspects, or in the alternative to some aspects, the method can further include changing a threshold for detecting the risk of an infection based on an input from a care provider or a clinician.

In a one hundred and seventeenth aspect, in addition to one or more of the preceding or following aspects, or in the alternative to some aspects, the method can further include using data regarding an activity level of the device wearer along with data regarding the physiological parameters to detect the risk of an infection.

In a one hundred and eighteenth aspect, in addition to one or more of the preceding or following aspects, or in the alternative to some aspects, the method can further include using geolocation data to characterize an activity level of the device wearer.

In a one hundred and nineteenth aspect, in addition to one or more of the preceding or following aspects, or in the alternative to some aspects, the method can further include using motion sensor data to characterize an activity level of the device wearer.

In a one hundred and twentieth aspect, in addition to one or more of the preceding or following aspects, or in the alternative to some aspects, the method can further include using microphone data to characterize an activity level of the device wearer.

In a one hundred and twenty-first aspect, in addition to one or more of the preceding or following aspects, or in the alternative to some aspects, the method can further include receiving data regarding physiological parameters from a separate wearable device.

In a one hundred and twenty-second aspect, in addition to one or more of the preceding or following aspects, or in the alternative to some aspects, the method can further include receiving data regarding the device wearer from a medical record system.

In a one hundred and twenty-third aspect, in addition to one or more of the preceding or following aspects, or in the alternative to some aspects, the method can further include evaluating changes in physical activity using data from the sensor package along with the physiological parameters to detect the risk of an infection.

In a one hundred and twenty-fourth aspect, in addition to one or more of the preceding or following aspects, or in the alternative to some aspects, the method can further include evaluating urination frequency using data from the sensor package along with the physiological parameters to detect the risk of an infection.

In a one hundred and twenty-fifth aspect, in addition to one or more of the preceding or following aspects, or in the alternative to some aspects, the method can further include exchanging data with a second ear-wearable infection sensor device.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Infections represent a substantial threat to human health. Infections can cause substantial direct harm as well as indirect harm such as through their impact on inflammation. In many cases, early medical intervention can be critical to achieving the best health outcomes.

Embodiments of ear-wearable device herein can be used to detect the risk of possible onset and/or presence of infections. Various embodiments of ear-wearable devices herein, including ear-wearable infection sensor devices, can analyze data from sensors to accurately identify the risk of possible or probable onset and/or presence of an infection.

Ear-wearable devices herein are uniquely capable of, and valuable for, detecting infection. This is because such devices, including those used as hearing assistance devices, are typically worn all the time (or nearly all the time) by device wearers. This means that infection can be detected rapidly after onset and can be done outside of a clinic. In addition, sensor data can be analyzed substantially continuously allowing changes that may indicate an infection to be more quickly and accurately recognized.

Embodiments herein can also include ear-wearable devices configured to operate in a first mode and second mode, wherein the first mode includes evaluating signals from sensors, to establish baseline values and the second mode includes monitoring signals from sensors to identify the risk of onset and/or presence of an infection.

Embodiments herein can also include ear-wearable devices configured to generate a set of data reflecting current physiological parameters and/or related data of a device wearer based on signals from sensors and/or data received from other devices and match the set of data against a plurality of predetermined patterns (which can include positive example patterns, negative example patterns, and the like) to determine whether the device wearer currently has an infection.

Figure 1:
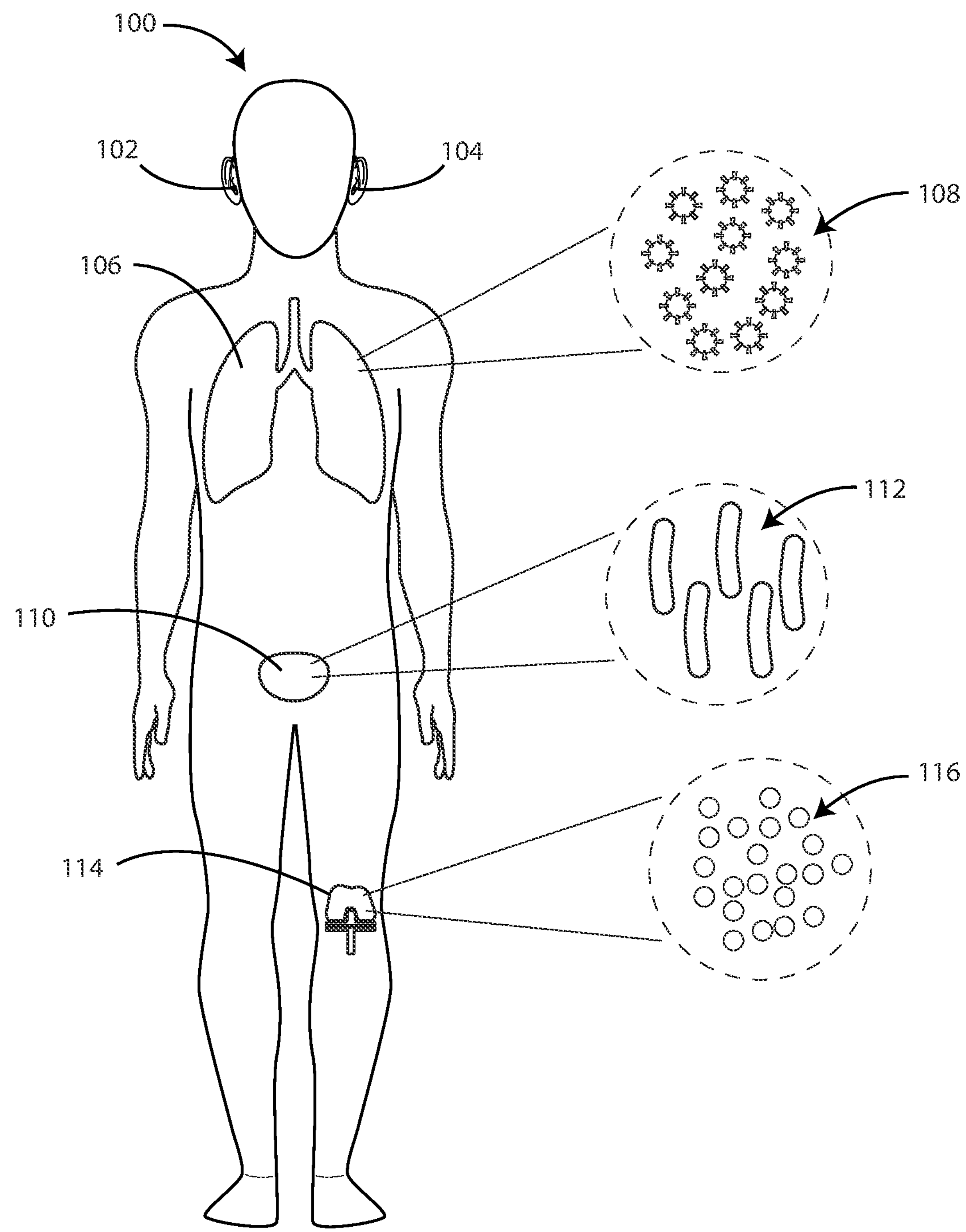
FIG. 1 is a schematic view of infection sensor devices and a device wearer in accordance with various embodiments herein.

Embodiments herein can also include ear-wearable devices configured to generate a set of data reflecting a current health status of a device wearer based on signals from one or more sensors and compare the set of data against stored data reflecting a previous health status of the device wearer and characterize an infection status of the device wearer based on a change from the previous health status to the current health status of the device wearer. Referring now to FIG. 1, a schematic view is shown of a device wearer 100 with ear-wearable infection sensor devices 102 and 104. The ear-wearable infection sensor devices 102 and 104 can detect various types of infections in various parts of the body. By way of example, FIG. 1 illustrates the lungs 106 of the device wearer 100 and a viral infection 108 therein. FIG. 1 also illustrates the bladder 110 of the device wearer 100 and a bacterial infection 112 therein. In some cases, a previous medical procedure such as the surgical implantation of a device may lead to an elevated risk of infection at the site of the implant. As such, FIG. 1 also illustrates an implanted device 114 (in the form of a replacement joint) and a staphylococcal infection 116 (as a specific type of bacterial infection) thereon. It will be appreciated that infections detected herein can include all types of infections a human may experience including, but not limited to, bacterial infections, viral infections, parasitic infections, fungal infections, protozoal infections, helminthic infections, and prion infections, and the like.

In various embodiments, the ear-wearable infection sensor devices 102, 104 can each include various components such as a control circuit, a microphone, a sensor package, and an electroacoustic transducer. The ear-wearable infection sensor devices 102, 104 can be configured to analyze data from the sensor package and/or the microphone to determine physiological parameters of the device wearer 100. The ear-wearable infection sensor devices 102, 104 can also be configured to evaluate the physiological parameters to detect the risk of presence of an infection. While two ear-wearable infection sensor devices are shown in FIG. 1, it will be appreciated that in some cases only a single ear-wearable infection sensor device may be used.

In various embodiments, the ear-wearable infection sensor device 102 can be configured to issue an alert or warning if a risk of infection is detected. The alert can be provided to the device wearer and/or to one or more third parties such as a care provider, clinician, or other responsible party. In some cases, the alert may take the form of an electronic data transmission. In some embodiments, an alert can be a video and/or an audio alert using components of the ear-wearable device such as an electroacoustic transducer or using components of another device. In some embodiments, the device and/or system can calculate a probability of an infection and/or a numerical value reflecting a probability of infection and can issue an alert if the probability or numerical value crosses a threshold value.

In various scenarios, embodiments here can also use other types of data beyond that related to physiological parameters to improve the accuracy of risk detection of an infection. Accuracy can be important as a device that issues too many false alerts or warnings of infection will soon be ignored. For example, devices herein can also use data regarding an activity level of a device wearer, movement data, geolocation data, microphone data, data from separate devices, medical record data, food and/or water intake data, urination frequency data, and the like to improve the accuracy of identification of an infection.

Many different types of data can be used by device and/or systems herein. In some cases, the data can originate with sensors of the device and/or system. In some cases, the data can originate with sensors of other devices or components can be transmitted to the devices and/or systems herein. In still other cases, the data may not be sensor data, but another type of data that may impact the accurate detection of a risk of infection, such as health data regarding the device wearer. While not intending to be bound by theory, patterns of data reflecting a greater number of data types can allow for greater infection detection accuracy than patterns of data reflecting fewer data types.

Figure 2:
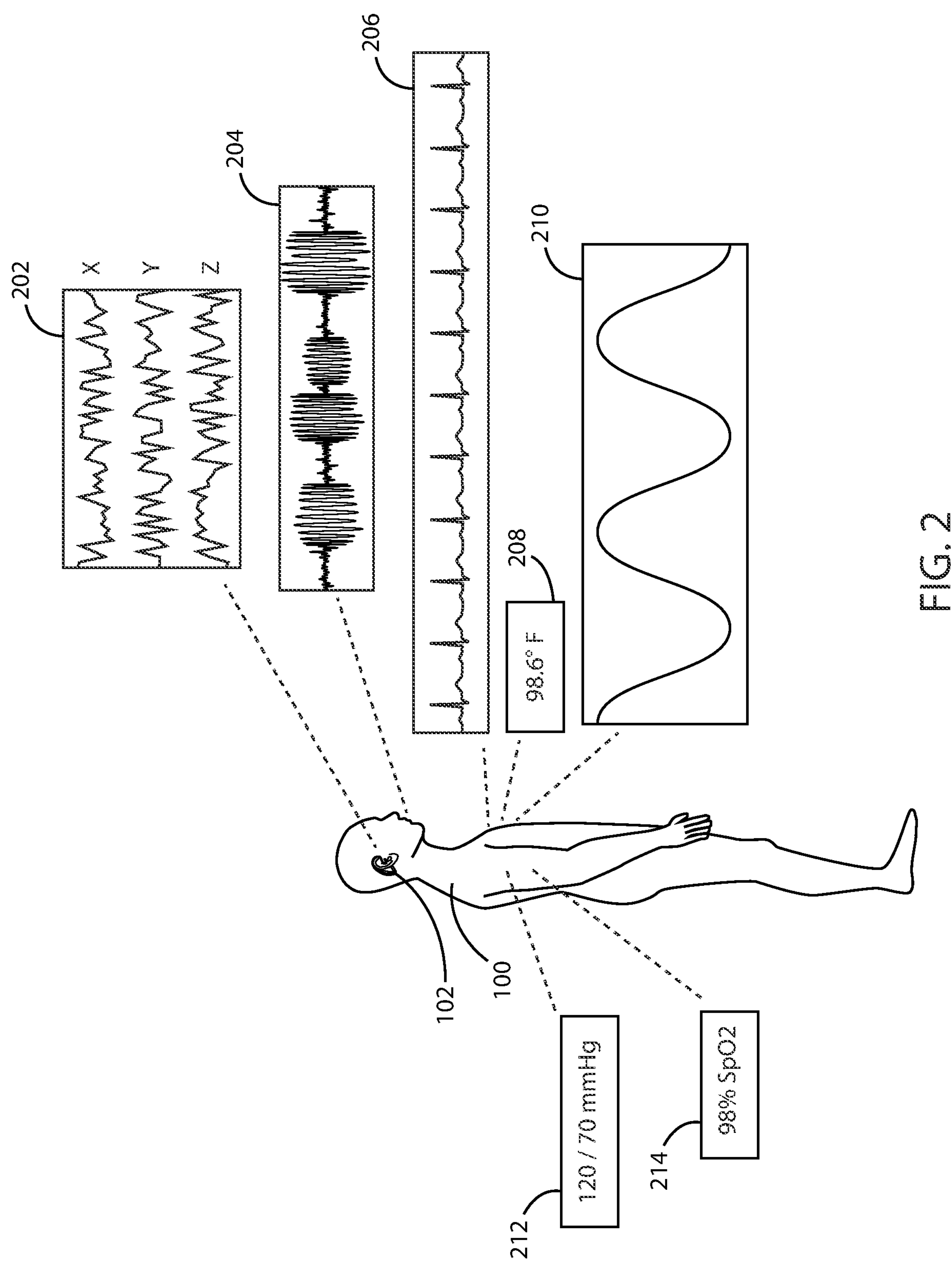
FIG. 2 is a schematic view of an infection sensor device and a device wearer in accordance with various embodiments herein.

Referring now to FIG. 2, a schematic view of an infection sensor device 102 and a device wearer 100 is shown in accordance with various embodiments herein. FIG. 2 shows some examples of data that can be used herein. Specifically, FIG. 2 shows motion sensor data 202, sound data 204, cardiac data 206, temperature data 208, respiration data 210, blood pressure data 212, and oxygen saturation (SpO2) data 214. Sound data 204 can reflect various types of things including, for example, voice data (such as the device wearer's voice), breathing sounds (as described further below), and other occurrences such as sneezing, coughing, and the like.

Various combinations of data reflecting physiological parameters can be used to identify an infection in accordance with embodiments herein. In some embodiments, the physiological parameters can include one or more of a respiration rate, a heart rate, and SpO2. In various scenarios, infection can be marked by a faster respiration rate with more shallow breaths. In various scenarios, infection can be marked by a slower or faster than normal heart rate. In various embodiments, infection can be marked by a reduced oxygen saturation (SpO2) value. In some embodiments, the physiological parameters used herein can include two or more of a respiration rate, a heart rate, and SpO2. In some embodiments, the physiological parameters used herein to detect infection can include all three of a respiration rate, a heart rate, and SpO2. In various embodiments, the physiological parameters used herein can also include a temperature. In general, core temperature increases with the presence of an infection.

Temporal aspects of the data and/or physiological parameters can also be evaluated. By way of example, in various embodiments, the ear-wearable infection sensor device 102 can be configured to evaluate a duration of a data change, such as a duration of a temperature data 208 elevation. In various embodiments, the ear-wearable infection sensor device 102 can be configured to evaluate a time course of a data change, such as a time course of a temperature data 208 elevation.

In some cases, infection may influence certain types of data and/or physiological parameters before others. Thus, in various embodiments, the ear-wearable infection sensor device 102 can be configured to evaluate a sequence of changes in the data and/or physiological parameters as part of evaluating the physiological parameters. For example, core temperature change associated with the onset of an infection may precede a change in other physiological parameters. As such, the device and/or system can be configured so that identifying that core temperature change has occurred before other changes results in a higher probability of infection being determined and/or a higher probability of subsequent actions being take such as issuing an alert.

In various embodiments, the ear-wearable infection sensor device 102 can be configured to evaluate breathing sounds. For example, in various embodiments, the ear-wearable infection sensor device 102 can be configured to analyze data from the microphone to evaluate breathing sounds of the device wearer 100 in combination with evaluating the physiological parameters to detect the risk of presence of the infection.

Characteristic breathing sounds can vary with the respiration cycle. For example, inspiration can sound different than expiration. In various embodiments, the ear-wearable infection sensor device 102 to evaluate breathing sounds at discrete points of a respiration cycle. Some types of breathing related sounds may be easier to identify at certain points of the respiration cycle. For example, the sounds crackling sounds (rales) associated with fluid in the lungs, which may be associated with an infection, can be more pronounced and easier to identify during inspiration. In some cases, breathing sounds can be evaluated at the same point in the cycle across multiple breathing cycles. In various embodiments, the ear-wearable infection sensor device and/or system can be configured to evaluate left-side versus right-side breathing sounds. For example, in embodiments where two ear-wearable infection sensor devices are used, with one on the right ear and one on the left ear, the spatial origin of sound can be identified and the system can distinguish between sounds reflecting infection on the right side versus the left side.

In various embodiments, the ear-wearable infection sensor device 102 can be configured to identify the occurrence of reflexes that may reflect the presence of an infection. By way of example, in some embodiments the ear-wearable infection sensor device 102 can be configured to identify a cough based on its unique sound signature using microphone data herein and/or in combination with data from a movement sensor coinciding with a coughing sound. In various embodiments, the ear-wearable infection sensor device 102 can be configured to distinguish between a wet cough (expelling of mucus) and a dry cough. For example, the device and/or system can evaluate the sound signature of an identified cough and using a pattern matching technique such as those described further below match against predetermined patterns reflecting a wet cough versus a dry cough. In various embodiments, the ear-wearable infection sensor device 102 can be configured to identify a sneeze. In some embodiments the ear-wearable infection sensor device 102 can be configured to identify a sneeze based on its unique sound signature using microphone data herein and/or in combination with data from a movement sensor coinciding with a coughing sound.

In various embodiments, the ear-wearable infection sensor device 102 can be configured to generate a sound and then record and/or evaluate received reflected sound. For example, the ear-wearable infection sensor device 102 can generate an ultrasonic sound and then record and/or evaluate received reflected sound. The ear-wearable infection sensor device 102 can include an inward facing microphone in order to pick up such reflected sounds. In some embodiments, the ear-wearable infection sensor device 102 can generate a sound at a frequency that is outside the range of normal human hearing and then record and/or evaluate received reflected sound. Infection can result in changes, such as fluid buildup and/or tissue stiffness that may change the properties of reflected sounds. Therefore, by evaluating the received, reflected sound, the device and/or system can detect changes that may reflect the onset or presence of an infection.

In various embodiments, the ear-wearable infection sensor device 102 can be configured to classify a set of data from at least one of the sensor package and the microphone into a category from amongst a set of categories. Details of exemplary classification techniques are provided in greater detail below. However, in various embodiments, the category reflects a probability of an infection. Therefore, the result of categorization can result in a determination of a probability of an infection. In various embodiments, the category reflects a severity of an infection. Therefore, the result of categorization can result in a determination of the severity of an infection. In various embodiments, the category reflects a type of an infection. Therefore, the result of categorization can result in a determination of the type of an infection.

In various embodiments, the ear-wearable infection sensor device 102 can be configured to match a set of data from at least one of the sensor package and the microphone against a plurality of predetermined patterns to determine infection status. In various embodiments, the ear-wearable infection sensor device 102 can be configured to match changes in data from at least one of the sensor package and the microphone against a plurality of predetermined patterns of changes in data to determine infection status. Sets of data (and/or changes in data) used for pattern matching can also include data other than that gathered by sensors of the device and/or system. For example, sets of data used for pattern matching can also include data from one or more secondary devices, from data sources such as resources in the cloud, from an API, or the like.

In various embodiments, the ear-wearable infection sensor device 102 can be configured to change a threshold for issuing an alert and/or determining the risk of presence of an infection based on data regarding one or more of the device wearer's health history (including, but not limited to, infection history), age, gender, weight, medication status, and BMI. For example, the threshold for determining that an infection is present for a patient with a record of previous infections may be set lower than an otherwise identical individual without a record of previous infections. Similarly, the threshold for determining that an infection is present for a patient with a recent surgical procedure may be set lower than an otherwise identical individual without a record of a recent surgical procedure.

Some changes in sensor data and/or physiological parameters may result from physical activity as opposed to the onset of infection. Thus, activity levels can be an important consideration when evaluating sensor data and/or physiological parameters to accurately detect infection. For example, both heart rate and respiration rate will rise with physical activity without any bearing on the presence of an infection. As such, taking into account physical activity can increase the accuracy of infection risk detection. In various embodiments, threshold values for detecting infection are increased during periods of higher detected activity to reduce false positives. In some embodiments, the device or system may suspend operations related to detecting infection and/or actions thereafter (such as issuing alerts) if physical activity above a threshold value is detected.

Figure 3:
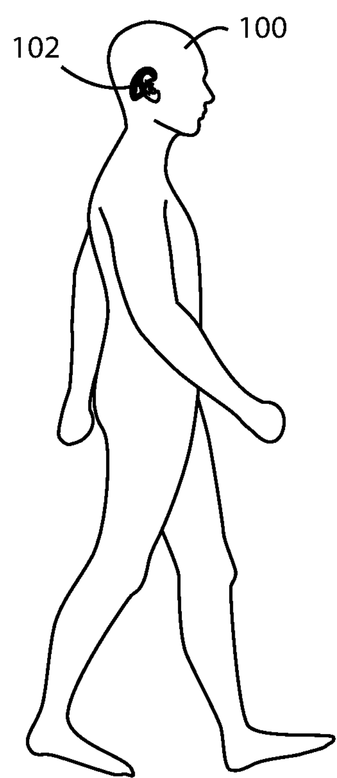
FIG. 3 is a schematic view of a device wearer with an infection sensor device in accordance with various embodiments herein.

Referring now to FIG. 3, a schematic view of a device wearer 100 with an infection sensor device 102 is shown in accordance with various embodiments herein. In various embodiments, the sensor package can include a motion sensor, wherein the ear-wearable infection sensor device 102 can be configured to evaluate physical activity of the device wearer 100 using signals from the motion sensor (motion data). The ear-wearable infection sensor device 102 can use signals from the motion sensor (and/or signals from another source that is indicative of physical activity of the device wearer) in combination with evaluating the physiological parameters to detect the risk of the presence of the infection.

In various embodiments, the ear-wearable infection sensor device 102 can be configured to evaluate the physiological parameters for the risk of the presence of infection while the device wearer 100 is in a resting state. For example, if the physical activity level of the device wearer exceeds a threshold value, then the device and/or system may enter a suspended operation mode where it does not evaluate the data and/or does not issue alerts upon the detection of possible infections. Conversely, if the physical activity level is below a threshold value, then the device and/or system enters an active operation mode where it evaluates the data and/or issues alerts upon the detection of risk of possible infections.

In various embodiments, the ear-wearable infection sensor device 102 can be configured to compare the physiological parameters reflecting the device wearer 100 in a resting state versus the device wearer 100 in a non-resting state. In this manner, the device and/or system can learn how physiological parameters are likely to change for a given individual and then later use this information to cancel out the effects of physical activity for a given individual when evaluating for the presence of an infection. As such, the device and/or system can record data and/or physiological parameters along with corresponding activity levels. Then, after sufficient data has been gathered, the device and/or system can process the data in order to identify the relationship between (or correlation) between activity levels and sensor or physiological parameter values. Then, during later operations, the device or system can cancel out the impact of activity on measured sensor or physiological parameter values based on current measurements of physical activity.

In some cases, posture may provide insights into optimal times to evaluate for the risk of the presence of an infection. For example, it can be advantageous to evaluate for the risk of an infection when the device wearer is seated or lying down, reflecting limited physical activity. In addition, in some cases sound can change with different postures. For example, when upright a breathing sound can appear one way, but when laying down a shift in fluid or pressure can make the sound appear differently. Therefore, it can be advantageous to control for the posture of the device wearer. As such, in various embodiments, the ear-wearable infection sensor device 102 can be configured to analyze data from the sensor package to determine a posture of the device wearer 100. In some embodiments, the sensor package can include an accelerometer which can be used to detect the direction of gravity. Based on the normal position of the ear-wearable devices with respect to the head, it can be determined whether the head is in a position consistent with lying down or not. If the posture meets preselected criteria, then the device or system can evaluate the data for the risk of an infection and/or issue alerts based upon the same. In some embodiments, the device or system can be configured to normalize data based on the determined posture in order to make comparisons and/or pattern identification or matching more accurate. In some embodiments, the device or system can be configured to index data based on the determined posture.

In some cases, geolocation data can be used to identify a beneficial time for evaluating the data for the risk of the presence of an infection and/or issuing alerts based upon the same. For example, the device or system can be configured to evaluate data for the risk of the presence of an infection with the device wearer is determined to be in their home. However, in some scenarios, geolocation can be used as a proxy for likely activity levels. For at least these applications, in various embodiments the ear-wearable infection sensor device 102 and/or system can be configured to use geolocation data to characterize an activity level of the device wearer 100.

In some cases, microphone data can be used to identify a beneficial time for evaluating the data for the risk of the presence of an infection and/or issuing alerts based upon the same. For example, the device or system can be configured to evaluate data for the risk of an infection when the microphone data indicates that the device wearer is in a quiet environment. In some cases, microphone data can be used as a proxy for likely activity levels. As such, in various embodiments, the ear-wearable infection sensor device 102 and/or system can be configured to use microphone data to characterize an activity level of the device wearer 100.

In various embodiments, the ear-wearable infection sensor device 102 can be configured to evaluate changes in physical activity using data from the sensor package along with the physiological parameters to detect the risk of the presence of an infection. If an individual is feeling ill, it is likely that their physical activity will decrease. As such, detecting reduced physical activity along with other characteristic changes associated with an infection can make it more likely that an infection is actually present. Changes in physical activity reflect data that can be evaluated as part of a set of data for pattern matching operations as described herein.

In various embodiments, the ear-wearable infection sensor device 102 can be configured to evaluate urination frequency using data from the sensor package along with the physiological parameters to detect the risk of the presence of an infection. In some cases, such as in the case of a bladder infection, urination frequency can increase. Changes in urination frequency can reflect data that can be evaluated as part of a set of data for pattern matching operations as described herein. Urination events can be detected based on a unique sound signature in microphone data using pattern matching or other techniques described herein.

Temperature can be an important piece of data to evaluate when detecting the risk of onset and/or presence of an infection. However, core temperature of an individual can fluctuate over time in the absence of an infection. For example, core temperature of an individual can fluctuate over time according to a circadian pattern. Thus, changes in temperature need to be considered carefully in accurately detecting the risk onset or presence of an infection.

Figure 4:
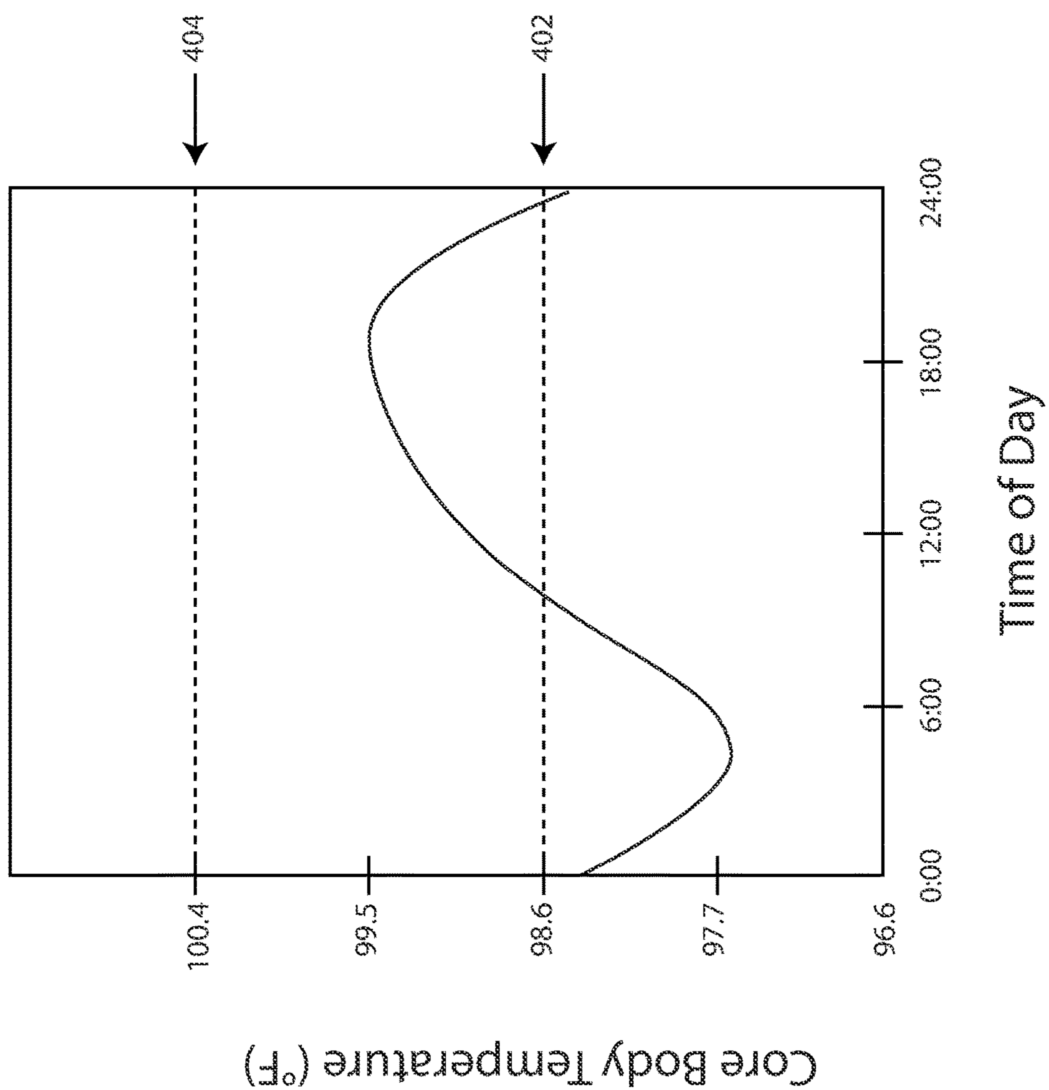
FIG. 4 is a schematic view of core temperature fluctuation over time in accordance with various embodiments herein.

Referring now to FIG. 4, a schematic view of core temperature 208 fluctuation over time is shown in accordance with various embodiments herein. FIG. 4 specifically shows an average baseline temperature 402 and a fever temperature 404. Fever temperature 404 can be defined as 100.4 degrees Fahrenheit. While the average baseline temperature 402 will generally vary somewhat across individuals, it follows a circadian pattern generally falling through the late evening and early morning hours reaching a low point just before normal waking hours and then rising from that point on into the early evening.

In various embodiments, the temperature 208 used by the system for detecting the risk of onset or presence of an infection reflects one or more of a real-time (instantaneous) temperature, a short-term temperature (such as a short-term temperature average), a long-term temperature (such as a long-term temperature average), or a circadian temperature (or circadian corrected temperature wherein circadian variation in temperature is canceled out).

In various embodiments, the ear-wearable infection sensor device 102 can be configured to identify a sub-fever level temperature elevation. For example, a rise in temperature above an average baseline temperature 402 can be significant for the detection of risk of infection even though it has not yet reached the threshold level required to be declared a fever. Similarly, in various embodiments, the ear-wearable infection sensor device 102 can be configured to identify a fever level or supra fever level temperature elevation. In various embodiments, the ear-wearable infection sensor device 102 can be configured to identify how rapidly a device wearer's core temperature rises from a baseline value (population or individual baseline) to a fever or supra-fever level temperature 404.

In various embodiments, the ear-wearable infection sensor device 102 can learn baseline values that are specific for a given individual. This can offer increased accuracy when detecting an infection. For example, the ear-wearable infection sensor device 102 can learn baseline values for temperature, heart rate, respiration rate, SpO2, and the like. In various embodiments, the ear-wearable infection sensor device 102 can be configured to gather baseline data over a first time period then calculate average values (or other statistical measures). The first time period can be a matter of seconds, minutes, hours, days, weeks, months or longer. In some embodiments, the baseline data can be gathered during or after a period of detected physical activity falling below a threshold value.

In various embodiments, the ear-wearable infection sensor device 102 can be configured to characterize and/or generate a baseline pattern based on the gathered baseline data (reflecting one or more types of data). This baseline pattern can then later be used to detect infection. For example, in various embodiments, the ear-wearable infection sensor device 102 can be configured to compare the baseline data or data pattern with real time data or a data pattern during a second time period.

Comparisons between baseline data or data patterns and real time data or data patterns can be performed in a manner so that the real time data is normalized based on various factors to allow for a more valid comparison. For example, in various embodiments, the comparison can be performed with the data normalized for circadian effects. In various embodiments, the ear-wearable infection sensor device can be configured to normalize the physiological parameters for estimated fatigue and stress. Fatigue and/or stress can be estimated based on movement data (amongst other types of data) of the device wearer over time preceding the time when the sensor data or physiological parameter data is gathered to detect infection. In various embodiments, the ear-wearable infection sensor device can be configured to normalize the physiological parameters for at least one of estimated anxiety and mental status. Anxiety and mental stress can be evaluated in various ways. In some embodiments, microphone data can be used to perform voice analysis to estimate anxiety and/or mental stress. In various embodiments, the ear-wearable infection sensor device can be configured to estimate at least one of pain and discomfort experienced by the device wearer based on data from at least one of the microphone and the sensor package. Pain and discomfort can be evaluated in various ways. In some embodiments, microphone data can be used to perform voice analysis to estimate pain and discomfort.

Figure 5:
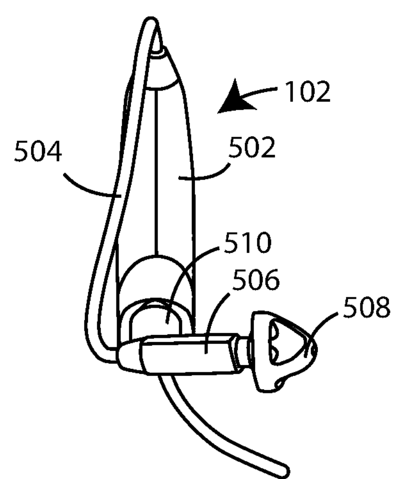
FIG. 5 is a schematic view of a wearable infection sensor device in accordance with various embodiments herein.

Referring now to FIG. 5, a schematic view of an ear-wearable device 102 is shown in accordance with various embodiments herein. The ear-wearable device 102 includes a housing 502 in which various components of the device can be housed. In this example, the ear-wearable device 102 also includes a battery compartment 510. However, some types of ear-wearable devices herein may lack a battery compartment, such as a device with a rechargeable battery. The ear-wearable device 102 also includes a cable 504 which connects to a receiver 506. The ear-wearable device 102 also includes an earbud 508.

It will be appreciated that while FIG. 5 illustrates one type of ear-wearable device (or ear-wearable sensor device) consistent with embodiments herein, many other types of ear-wearable devices are also contemplated. The term "ear-wearable device" as used herein can include devices that can aid a person with impaired hearing. The term "ear-wearable device" shall also refer to devices that can produce optimized or processed sound for persons with normal hearing. Ear-wearable devices herein can include hearing assistance devices. Ear-wearable devices herein can include, but are not limited to, behind-the-ear (BTE), in-the ear (ITE), in-the-canal (ITC), invisible-in-canal (ITC), receiver-in-canal (RIC), receiver in-the-ear (RITE) and completely-in-the-canal (CIC) type hearing assistance devices. In some embodiments, the ear-wearable device can be a hearing aid falling under 21 C.F.R. § 801.420. In another example, the ear-wearable device can include one or more Personal Sound Amplification Products (PSAPs). In another example, the ear-wearable device can include one or more cochlear implants, cochlear implant magnets, cochlear implant transducers, and cochlear implant processors. In another example, the hearing assistance device can include one or more "hearable" devices that provide various types of functionality. In other examples, ear-wearable devices can include other types of devices that are wearable in, on, or in the vicinity of the user's ears. In other examples, ear-wearable devices can include other types of devices that are implanted or otherwise osseointegrated with the user's skull; wherein the device is able to facilitate stimulation of the wearer's ears via the bone conduction pathway. In another example, the hearing assistance device can include an auditory brainstem implant, a cranial nerve (e.g., CN VIII) implant, and the like.

Figure 6:
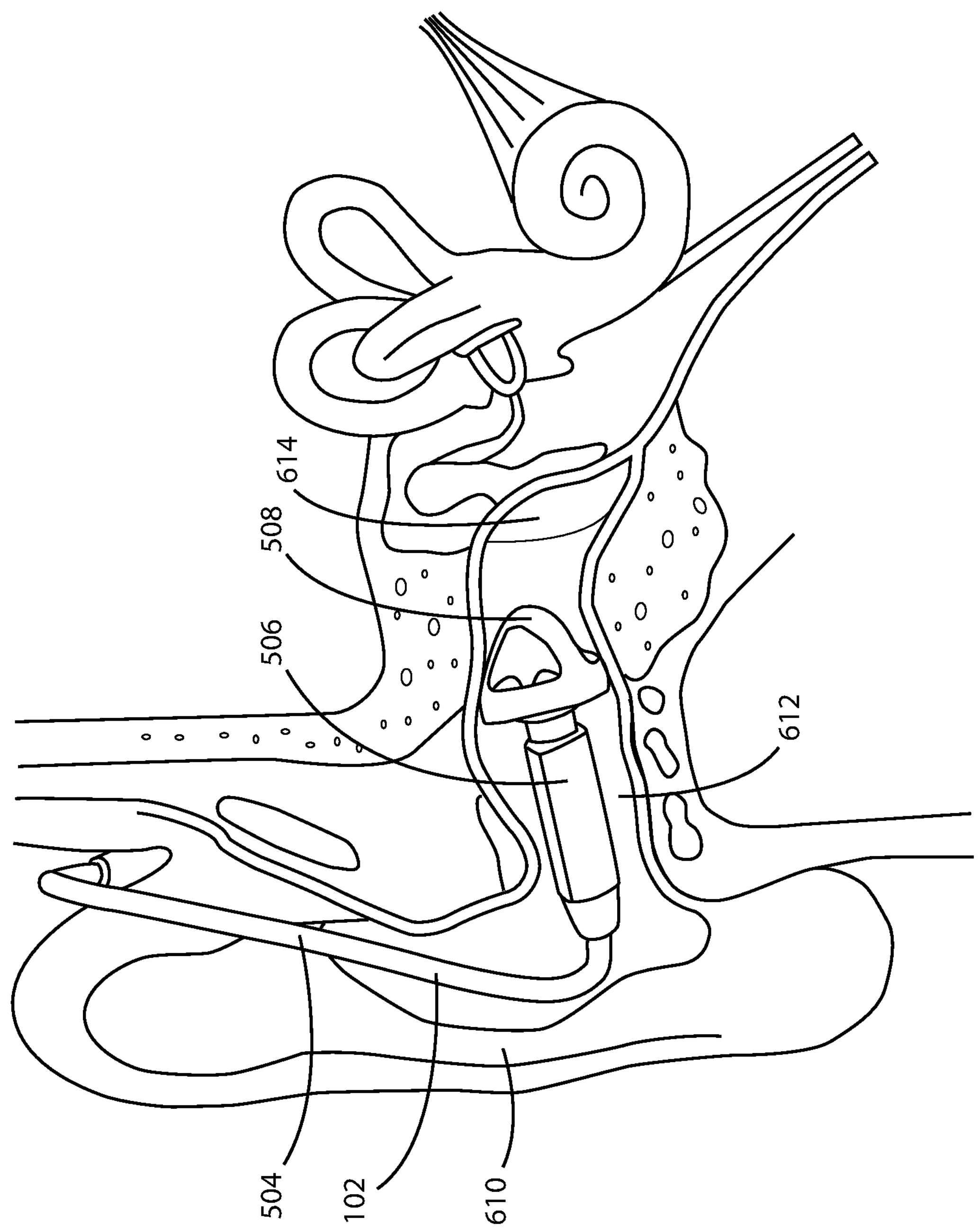
FIG. 6 is a schematic view of an infection sensor device within the ear of a wearer in accordance with various embodiments herein.
Figure 7:
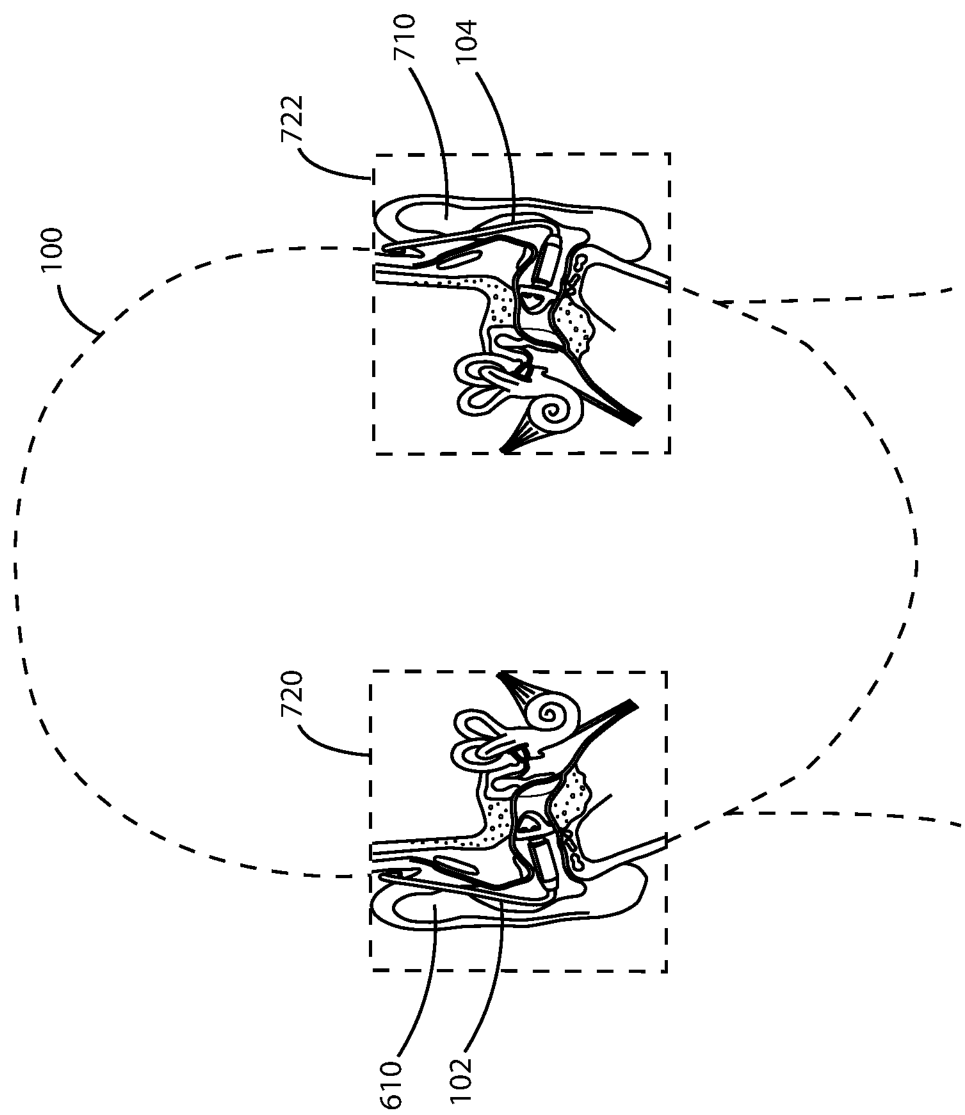
FIG. 7 is a schematic view of right and left sides of a device wearer in accordance with various embodiments herein.

Referring now to FIG. 6, a schematic view of the ear-wearable device 102 is shown with the device fitted in the ear of a device wearer. The significant portions of the ear, in this view, include pinna 610, ear canal 612, and tympanic membrane 614. As before, the ear-wearable device 102 includes a cable 504 connecting to a receiver 506. The ear-wearable device 102 also includes an earbud 508. Referring now to FIG. 7, a schematic view of right and left sides of a device wearer 100 is shown in accordance with various embodiments herein. The right side 720 device wearer 100 includes the right pinna 610 and an ear-wearable infection sensor device 102 therein. The left side 722 of the device wearer 100 is also shown including a left pinna 710 and a second ear-wearable infection sensor device 104.

In some embodiments herein, where two ear-wearable devices are used, the ear-wearable devices can replicate each other's functionality and/or operations such that a check can placed upon determinations of an infection being present. For example, if one device through its operations determines that an infection is likely present and the other device through its redundant operations does not determine that an infection is likely present then the devices can exchange such data and, to reduce false positives, may not take actions associated with an infection being detected (such as not sending an alert or other notification of a possible infection). However, if maximum sensitivity is desired at the risk of more false positives, the system can operate in a mode where it determines that an infection is likely present if either of the two devices independently determines that an infection is likely present. In some embodiments, the devices may not operate redundantly with respect to infection risk detection. For example, to conserve battery life, a duty-cycle like process can take place where one device is monitoring for an infection during some time periods and the other device is monitoring for an infection during other time periods. In some embodiments, the two devices can include the same sensor package and therefore be capable of producing the same types of data. However, in other embodiments, the two devices can include different sensor packages and therefore be capable of producing different types of data.

Figure 8:
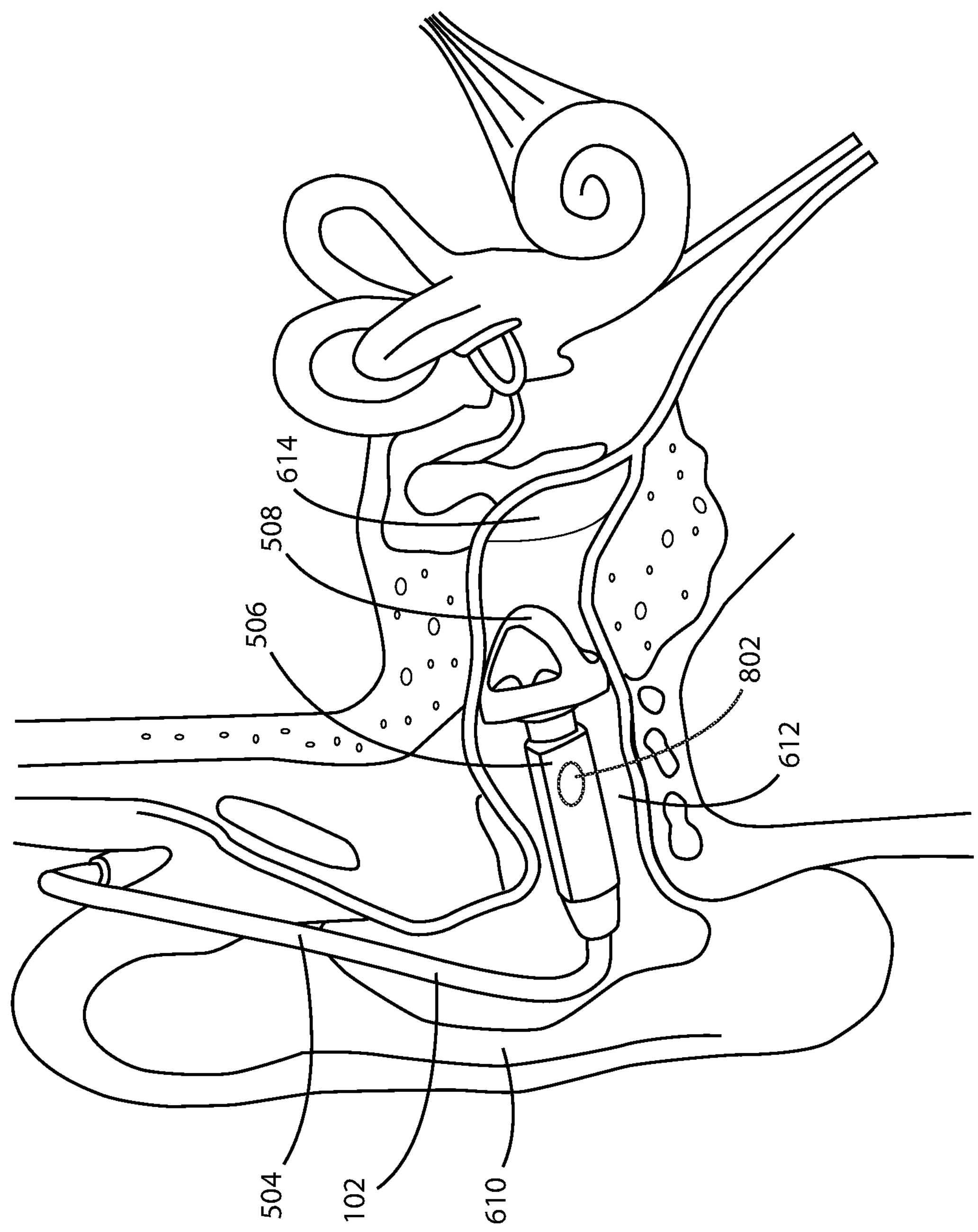
FIG. 8 is a schematic view of an infection sensor device within the ear of a wearer in accordance with various embodiments herein.

Sensors herein can be disposed in various places. In some embodiments, sensors can be configured to be within a housing of a device herein. In some embodiments, sensors can be configured to be on or within other components of the devices herein. In some embodiments, sensors can be configured so that they are within the ear canal of the device wearer when the device is being worn. Referring now to FIG. 8, a schematic view of an infection sensor device within the ear of a wearer is shown in accordance with various embodiments herein. FIG. 8 is generally similar to FIG. 6. However, in this embodiment, the sensor package of the device includes a temperature sensor 802 that can be mounted on or adjacent to a component within the ear canal 612 such as the receiver 506. Thus, in various embodiments, the temperature sensor 802 can be configured for placement within the ear canal 612. Exemplary types of temperature sensors are described in greater detail below.

Orthostatic hypotension can be a useful condition to detect when evaluating the device wearer for the risk of the presence of an infection. Orthostatic hypotension is a transient form of low blood pressure that happens when you stand up from sitting or lying down. Some types of infection can result in dilation of blood vessels. As such, patients experiencing an infection can be more likely to exhibit orthostatic hypotension than are patients who are not experiencing an infection. Thus, the occurrence of orthostatic hypotension can be used as data as a part of identifying an infection. Various devices and/or systems herein can include pressure sensors that can be used to measure blood pressure. In addition, the action of standing up can be identified based on characteristic motion sensor data. Detecting an occurrence of transient hypotension coinciding with the action of standing up can be determined to be an occurrence of orthostatic hypotension.

Figure 9:
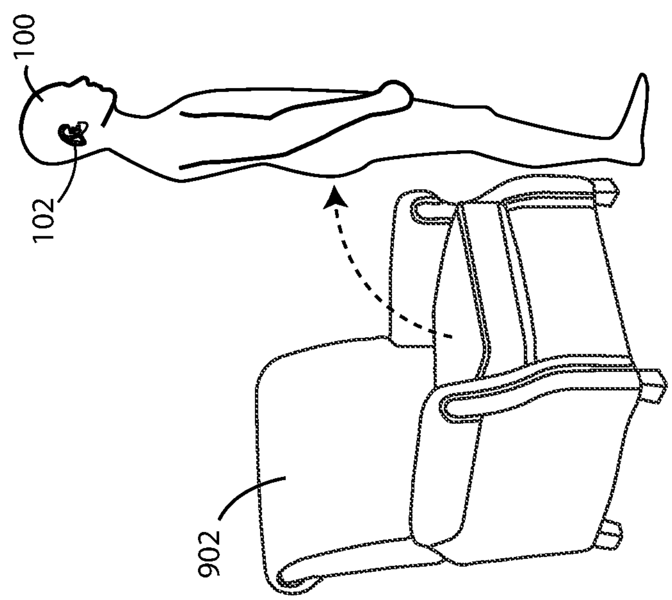
FIG. 9 is a schematic view of a device wearer rising from a chair in accordance with various embodiments herein.

Referring now to FIG. 9, a schematic view of a device wearer 100 rising from a chair 902 is shown in accordance with various embodiments herein. FIG. 9 shows an ear-wearable infection sensor device 102. In various embodiments herein, the device 102 and/or system can be used to detect transient hypotension that may occur while the device wearer 100 is standing up or shortly thereafter. To facilitate such detection, the sensor package of the ear-wearable infection sensor device 102 can include a pressure sensor and a motion sensor, wherein the ear-wearable infection sensor device 102 can be configured to detect orthostatic hypotension using data from the pressure sensor and the motion sensor. In some embodiments, the sensor package of the ear-wearable infection sensor device 102 can include a PPG sensor and a change in blood pressure can be detected using the PPG sensor waveform.

Figure 10:
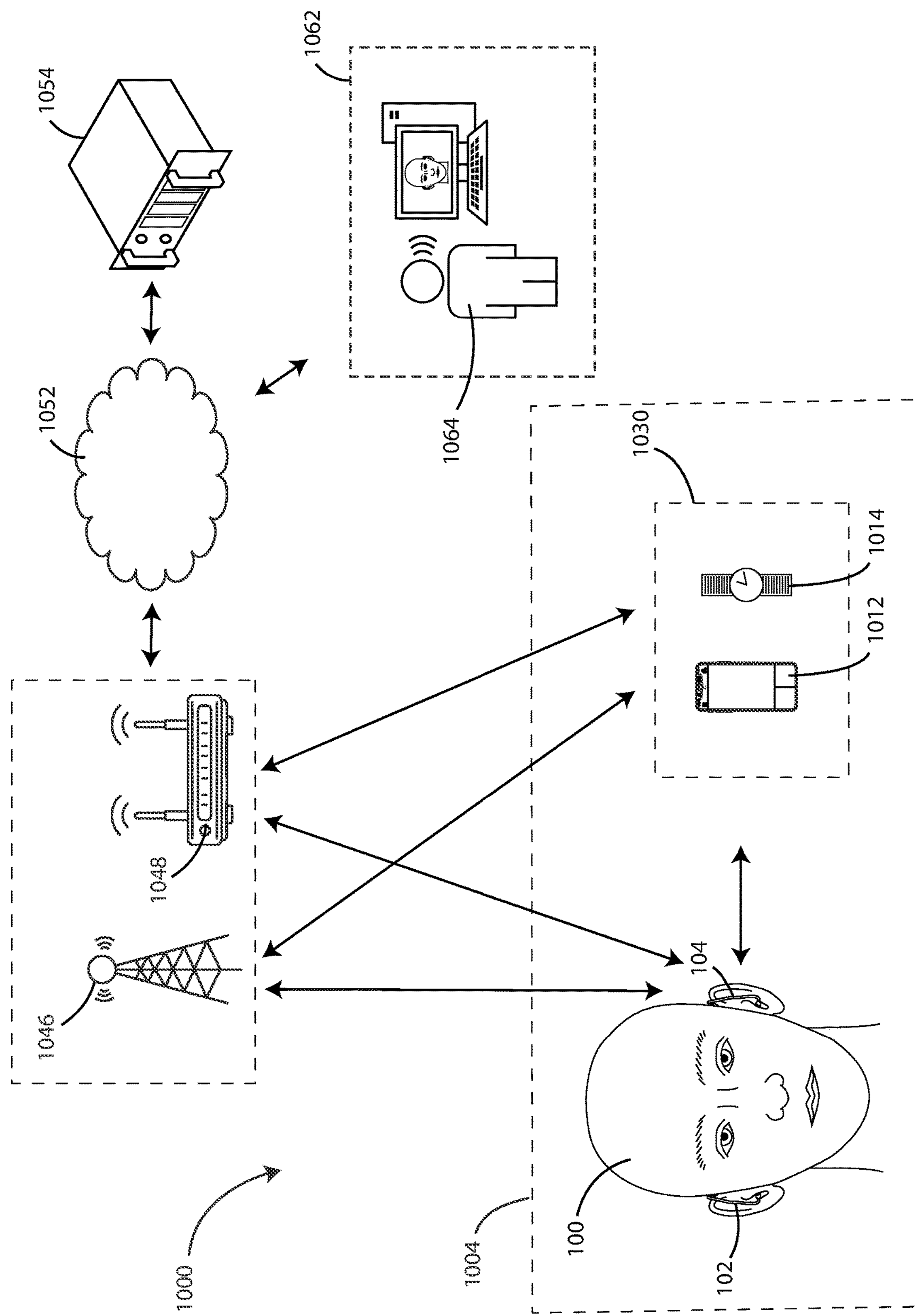
FIG. 10 is a schematic view of various components of a system in accordance with various embodiments herein.

It will be appreciated that systems herein can include and/or interface with many different devices or components. Referring now to FIG. 10, a schematic view of various components of a system 1000 is shown in accordance with various embodiments herein. A local environment 1004 can include the device wearer 100 along with an ear-wearable infection sensor device 102 and a second ear-wearable infection sensor device 104. Various accessory devices 1030 can also be associated with the device wearer 100 and/or can contain or gather data regarding the device wearer 100 in the local environment 1004. The accessory devices 1030 can include, but are not limited to, a smart phone 1012 and a wearable device 1014, amongst others. Various data communication elements can be used to convey data transmissions to or from device and/or system herein. By way of example, FIG. 10 shows a cell tower 1046 and a router 1048, each of which can be used to convey data communications to or from devices and/or system components herein. In some embodiments, data communications can be conveyed to or from the cloud 1052. The cloud 1052 can include various resources such as a remote server 1054 (which could be real or virtual) as well as other processing and/or data storage devices (real or virtual). In some embodiments, processing steps herein of data can be performed in the cloud 1052. In some embodiments, data can be retrieved from the cloud 1052 (and/or a medical record system that can be in or communicate through the cloud 1052 or another data network) and provided to devices and/or systems herein such as medical record data to allow access to health information regarding the device wearer. In various embodiments, the ear-wearable infection sensor device 102 can specifically be configured to receive information regarding previous infections of a device wearer 100.

FIG. 10 also shows a remote environment 1062. The remote environment 1062 can include a third party 1064. The third party 1064 can be a recipient of alerts sent in accordance with embodiments herein. The third party 1064 can be a care provider, a clinician, a family member, or the like. In various embodiments, the ear-wearable infection sensor device 102 can be configured to change a threshold for detecting the risk of the presence of an infection based on an input from a third party 1064, such as a care provider or a clinician.

Accessory devices (or secondary devices) can be useful sources of data in accordance with embodiments herein. By way of example, accessory devices, such as wearable devices can gather cardiac data, respiration data, blood pressure data, sound data, temperature data, SpO2 data, and the like. In various embodiments, the ear-wearable infection sensor device 102 can be configured to receive data regarding physiological parameters from a separate wearable device 1014.

In various embodiments, the ear-wearable infection sensor device 102 can be receive information from a secondary device regarding sputum. In some embodiments, a secondary device, such as smart phone with a camera can be pointed at the sputum of the device wearer and can gather data about the same including color data and, in some cases, data regarding the consistency and/or viscosity thereof. Such data can be conveyed to the ear-wearable infection sensor device 102 and used as a part of the data set for determining whether an infection is present.

In various embodiments, the ear-wearable infection sensor device 102 can be configured to instruct the device wearer 100 to hold an accessory device against their chest if an infection can be detected. In this scenario, a microphone of the accessory device can be used to detect sounds from within the device wearer's chest which can be used as a part of the data set for determining whether an infection is present. In some embodiments, after the accessory device is held against the chest then it can emit a sound (such as described elsewhere herein) and the reflected sound can be used as a part of the data set for determining whether an infection is present.

In various embodiments, location (such as geolocation) of the device wearer can be used in various ways, including as a part of the data set for determining whether an infection is present. In some embodiments, geolocation can be used to help identify beneficial times during which to try to evaluate data to identify the risk of the onset or presence of an infection. However, geolocation can also be used in other ways. For example, if an outbreak of foodborne illness is associated with a particular geolocation such as a particular restaurant, it can be valuable to know whether the device wearer has visited that location. As one example, threshold values for identifying the risk of the onset or presence of an infection can be varied based on geolocations visited by the device wearer, and, as an example, threshold values can be lowered if the device wearer has visited a geolocation associated with foodborne illness/infections.

Figure 11:
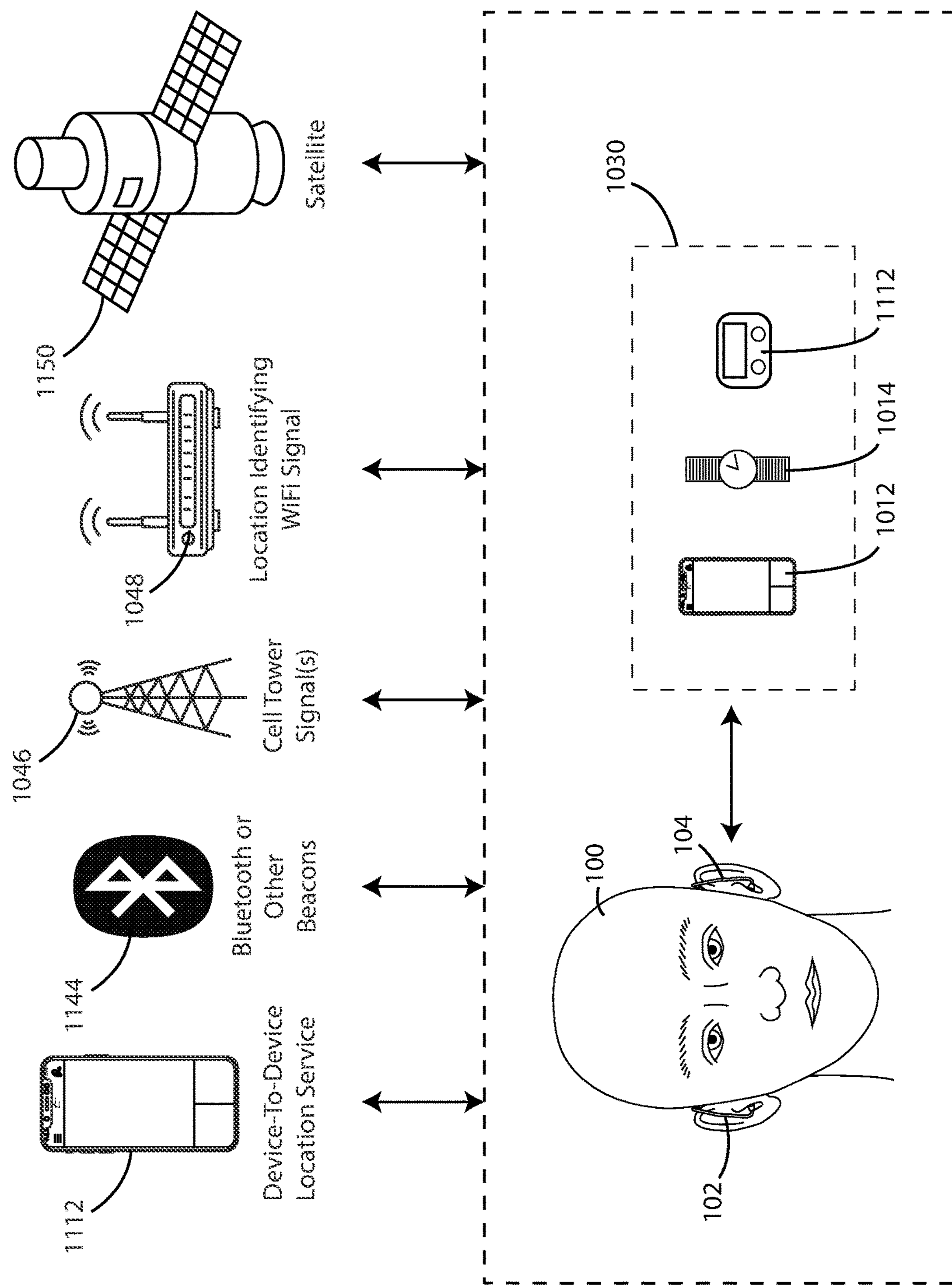
FIG. 11 is a schematic view of components used to derive location in accordance with various embodiments herein.

Referring now to FIG. 11, a schematic view of components used to derive location is shown in accordance with various embodiments herein. FIG. 11 shows a device wearer 100 along with an ear-wearable infection sensor device 102 and a second ear-wearable infection sensor device 104. FIG. 11 shows accessory devices 1030 (or secondary devices), which can include a smart phone 1012, a wearable device 1014, and an external monitoring device 1112. Geolocation can be derived in various ways. In some embodiments, geolocation can be derived based on a device-to-device location service such as illustrated by interface with third party smart phone 1102. Geolocation can also be derived based on interfacing with Bluetooth or other beacons 1144. Geolocation can also be derived based on interfacing with a wireless communications site, such as a cellular communication tower 1046 or a router 1048. Geolocation can also be derived based on signals from a geolocation satellite 1150.

In various embodiments, the ear-wearable infection sensor device 102 can be configured to change a threshold for detecting the risk or the presence of an infection based on geolocation data reflecting past locations of the device wearer 100.

In various embodiments, the ear-wearable infection sensor device 102 can be configured to receive and utilize geographic infection trend data. For example, if the device wearer is in, or has been in, an area experiencing a higher level of infections, then, for example, threshold values for identifying the risk of onset or presence of an infection can be varied accordingly.

In various embodiments, the ear-wearable infection sensor device 102 can be configured to receive and utilize seasonal infection trend data. For example, threshold values for identifying the risk of onset or presence of an infection can be varied based on current season infection trends. If, for example, infections of a given type peak during a certain season, then threshold values for identifying the risk of onset or presence of that type of infection can be varied accordingly during that season.

Figure 12:
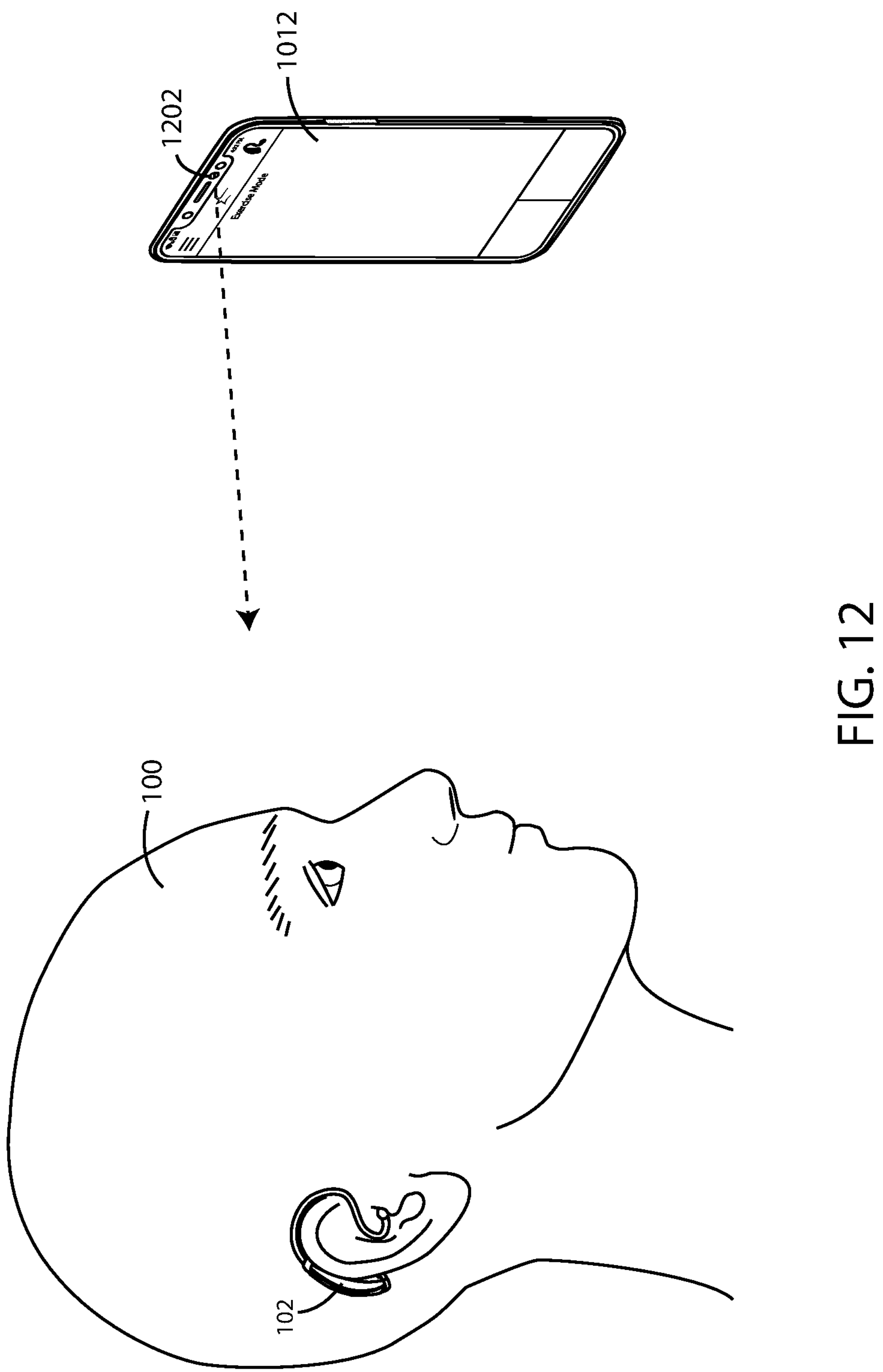
FIG. 12 is a schematic view of a device wearer with an infection sensor device and an accessory device in accordance with various embodiments herein.

Referring now to FIG. 12, a schematic view of a device wearer 100 with an infection sensor device 102 and an accessory device is shown in accordance with various embodiments herein. FIG. 12 also shows a smart phone 1012. The smart phone 1012 includes a camera 1202. The camera 1202 can be focused back at the device wearer 100 and thus serve as an optical color sensor to detect the color of the device wearer's skin. Some types of infections may be associated with changes in the device wearer's skin color. As such, the optical color sensor can be used to provide additional data that can be used to identify an infection. In various embodiments, the ear-wearable infection sensor device 102 can be configured to evaluate a real-time skin color compared with a baseline skin color for the device wearer 100. In various embodiments, the ear-wearable infection sensor device 102 can be configured to instruct the device wearer 100 to look at an accessory device with a camera 1202 to aid in detecting an infection.

Input from the device wearer can also be valuable in determining the risk of presence or onset of an infection. As an example, in various embodiments, the ear-wearable infection sensor device 102 can be configured to query the device wearer 100 regarding how they feel and then receive and record their response. The response received from the device wearer can be used as a part of the data set for determining whether an infection is present.

Figure 13:
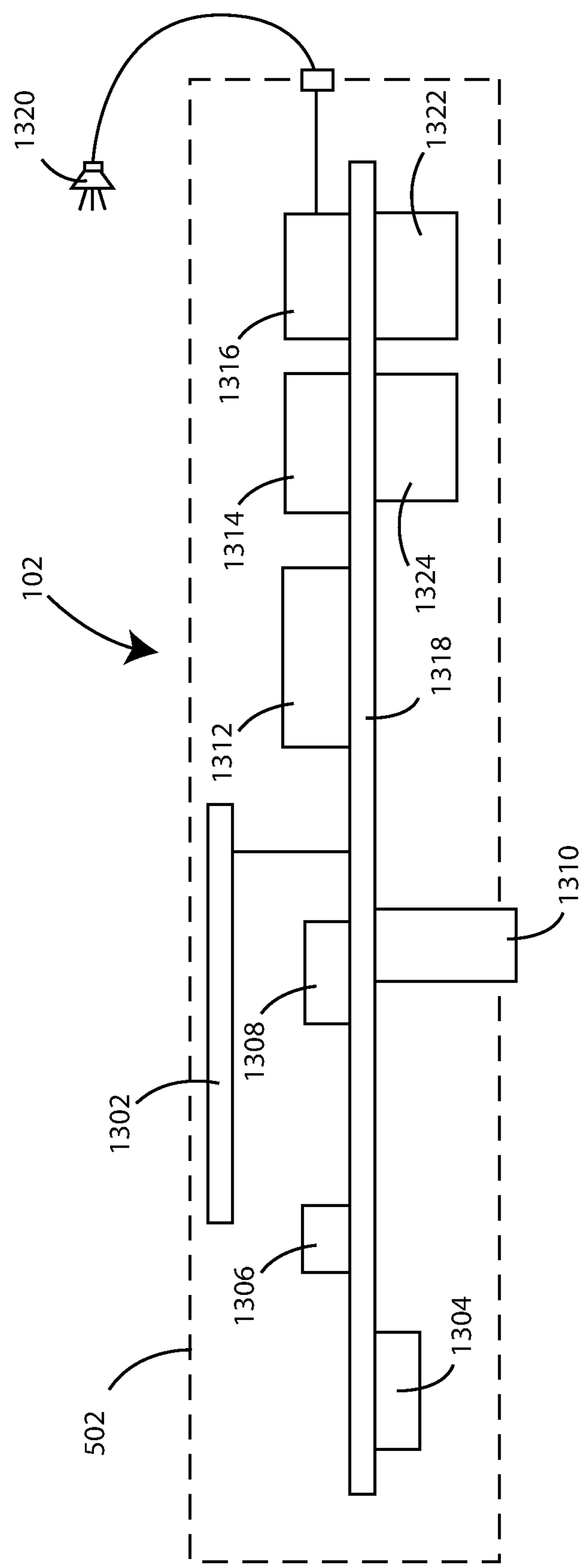
FIG. 13 is a schematic view of components of an infection sensor device in accordance with various embodiments herein.

Ear-wearable devices herein can include many different physical components. Referring now to FIG. 13, a schematic block diagram is shown illustrating various components of an ear-wearable device in accordance with various embodiments herein. It will be appreciated that many of these components can be integrated in an integrated circuit, such as with a system-on-a-chip (SOC) integration or can exist as separate components. The block diagram of FIG. 13 represents a generic ear-wearable device for purposes of illustration. The ear-wearable device 102 shown in FIG. 13 includes several components electrically connected to a flexible mother circuit 1318 (e.g., flexible mother board) which is disposed within housing 502. A power supply circuit 1304 can include a battery and can be electrically connected to the flexible mother circuit 1318 and provides power to the various components of the ear-wearable device 102. One or more microphones 1306 are electrically connected to the flexible mother circuit 1318, which provides electrical communication between the microphones 1306 and a digital signal processor (DSP) 1312. Among other components, the DSP 1312 incorporates or is coupled to audio signal processing circuitry configured to implement various functions described herein. A sensor package 1314 can be coupled to the DSP 1312 via the flexible mother circuit 1318. The sensor package 1314 can include one or more different specific types of sensors such as those described in greater detail below. One or more user switches 1310 (e.g., on/off, volume, mic directional settings) are electrically coupled to the DSP 1312 via the flexible mother circuit 1318. In some embodiments, a sensor package 1314 can be separated into a different housing or unit that is configured to be placed within the ear canal.

An audio output device 1316 is electrically connected to the DSP 1312 via the flexible mother circuit 1318. In some embodiments, the audio output device 1316 comprises a speaker (coupled to an amplifier). In other embodiments, the audio output device 1316 comprises an amplifier coupled to an external receiver 1320 adapted for positioning within an ear of a wearer. The external receiver 1320 can include an electroacoustic transducer, speaker, or loudspeaker. The ear-wearable device 102 may incorporate a communication device 1308 coupled to the flexible mother circuit 1318 and to an antenna 1302 directly or indirectly via the flexible mother circuit 1318. The communication device 1308 can be a Bluetooth® transceiver, such as a BLE (Bluetooth® low energy) transceiver or other transceiver(s) (e.g., an IEEE 802.11 compliant device). The communication device 1308 can be configured to communicate with one or more external devices, such as those discussed previously, in accordance with various embodiments. In various embodiments, the communication device 1308 can be configured to communicate with an external visual display device such as a smart phone, a video display screen, a tablet, a computer, a television, a virtual or augmented reality, a hologram, or the like.

In various embodiments, the ear-wearable device 102 can also include a control circuit 1322 and a memory storage device 1324. The control circuit 1322 can be in electrical communication with other components of the device. The control circuit 1322 can execute various operations, such as those described herein. The control circuit 1322 can include various components including, but not limited to, a microprocessor, a microcontroller, an FPGA (field-programmable gate array) processing device, an ASIC (application specific integrated circuit), or the like. The memory storage device 1324 can include both volatile and non-volatile memory. The memory storage device 1324 can include ROM, RAM, flash memory, EEPROM, SSD devices, NAND chips, and the like. The memory storage device 1324 can be used to store data from sensors as described herein and/or processed data generated using data from sensors as described herein.

In various embodiments, a spatial location determining circuit (or geolocation circuit) can be included and can take the form of an integrated circuit that can include components for receiving signals from GPS, GLONASS, BeiDou, Galileo, SBAS, WLAN, BT, FM, and/or NFC type protocols.

Methods

Many different methods are contemplated herein. In an embodiment, a method of detecting an infection using an ear-wearable device is included, the method can include analyzing data from a sensor package of the ear-wearable device to determine physiological parameters of a device wearer and evaluating the physiological parameters to detect a risk of or likely presence of an infection.

In an embodiment of the method, the physiological parameters can include at least one of a respiration rate, a heart rate, and SpO2. In an embodiment of the method, the physiological parameters can further include a temperature.

In an embodiment, the method can further include evaluating a duration of a temperature elevation. In an embodiment, the method can further include evaluating a time course of a temperature elevation.

In an embodiment, the method can further include evaluating a sequence of changes in the physiological parameters as part of evaluating the physiological parameters.

In an embodiment, the method can further include analyzing data from the microphone to evaluate breathing sounds of the device wearer in combination with evaluating the physiological parameters to detect the risk of or likely presence of the infection.

In an embodiment, the method can further include evaluating physical activity of the device wearer using signals from the motion sensor in combination with evaluating the physiological parameters to detect the risk of or likely presence of the infection.

In an embodiment, the method can further include detecting orthostatic hypotension using data from a pressure sensor and a motion sensor.

In an embodiment, the method can further include evaluating the physiological parameters while the device wearer is in a resting state. In an embodiment, the method can further include comparing the physiological parameters reflecting the device wearer in a resting state versus the device wearer in a non-resting state.

In an embodiment, the method can further include gathering baseline data over a first time period. In an embodiment of the method, gathering baseline data over a first time period further comprises characterizing a baseline pattern based on the gathered baseline data. In an embodiment, the method can further include comparing the baseline data with real time data during a second time period. In an embodiment, the method can further include normalizing the real time data based on circadian effects.

In an embodiment, the method can further include gathering baseline data after a period of detected physical activity falling below a threshold value.

In an embodiment, the method can further include identifying a sub-fever level temperature elevation. In an embodiment, the method can further include identifying a fever level temperature elevation.

In an embodiment, the method can further include normalizing the physiological parameters for estimated fatigue and stress. In an embodiment, the method can further include normalizing the physiological parameters for at least one of estimated anxiety and mental status. In an embodiment, the method can further include estimating at least one of pain and discomfort experienced by the device wearer based on data from at least one of the microphone and the sensor package.

In an embodiment, the method can further include evaluating breathing sounds. In an embodiment, the method can further include identifying a cough. In an embodiment, the method can further include distinguishing between a wet cough and a dry cough. In an embodiment, the method can further include evaluating breathing sounds at discrete points of a respiration cycle. In an embodiment, the method can further include evaluating left-side versus right-side breathing sounds. In an embodiment, the method can further include identifying a sneeze.

In an embodiment, the method can further include receiving and utilizing seasonal infection trend data. In an embodiment, the method can further include receiving and utilizing geographic infection trend data.

In an embodiment, the method can further include receiving information regarding previous infections of a device wearer.

In an embodiment, the method can further include receiving information from a secondary device regarding sputum.

In an embodiment, the method can further include generating a sound and recording received reflected sound.

In an embodiment, the method can further include evaluating a real-time skin color compared with a baseline skin color for the device wearer.

In an embodiment, the method can further include analyzing data from the sensor package to determine a posture of the device wearer.

In an embodiment, the method can further include classifying a set of data from at least one of the sensor package and the microphone into a category from amongst a set of categories. In an embodiment, the method can further include matching a set of data from at least one of the sensor package and the microphone against a plurality of predetermined patterns to determine infection status.

In an embodiment, the method can further include matching changes in data from at least one of the sensor package and the microphone against a plurality of predetermined patterns of changes in data to determine infection status.

In an embodiment, the method can further include querying the device wearer regarding how they feel.

In an embodiment, the method can further include issuing an alert if a risk of infection is detected.

In an embodiment, the method can further include instructing the device wearer to look at an accessory device with a camera if a possible infection is detected.

In an embodiment, the method can further include instructing the device wearer to hold an accessory device against their chest if a possible infection is detected.

In an embodiment, the method can further include changing a threshold for detecting the risk or likely presence of an infection based on data regarding one or more of the device wearer health history, age, gender, weight, medication status, and BMI. In an embodiment, the method can further include changing a threshold for detecting the risk or likely presence of an infection based on data regarding previous infections experienced by the device wearer. In an embodiment, the method can further include changing a threshold for detecting the risk or likely presence of an infection based on data regarding previous surgical procedures experienced by the device wearer. In an embodiment, the method can further include changing a threshold for detecting the risk or likely presence of an infection based on geolocation data reflecting past locations of the device wearer. In an embodiment, the method can further include changing a threshold for detecting the risk or likely presence of an infection based on an input from a care provider or a clinician.

In an embodiment, the method can further include using data regarding an activity level of the device wearer along with data regarding the physiological parameters to detect the risk or likely presence of an infection.

In an embodiment, the method can further include using geolocation data to characterize an activity level of the device wearer. In an embodiment, the method can further include using motion sensor data to characterize an activity level of the device wearer. In an embodiment, the method can further include using microphone data to characterize an activity level of the device wearer.

In an embodiment, the method can further include receiving data regarding physiological parameters from a separate wearable device.

In an embodiment, the method can further include receiving data regarding the device wearer from a medical record system.

In an embodiment, the method can further include evaluating changes in physical activity using data from the sensor package along with the physiological parameters to detect the presence of an infection.

In an embodiment, the method can further include evaluating urination frequency using data from the sensor package along with the physiological parameters to detect the presence of an infection.

In an embodiment, the method can further include exchanging data with a second ear-wearable infection sensor device.

Pattern Identification and Matching

It will be appreciated that in various embodiments herein, a device or a system can be used to detect an onset or presence of an infection. Patterns indicative of the onset or presence of an infection can be detected in various ways. Some techniques are described elsewhere herein, but some further examples will now be described.

As merely one example, one or more sensors can be operatively connected to a controller (such as the control circuit described in FIG. 13) or another processing resource (such as a processor of another device or a processing resource in the cloud). The controller or other processing resource can be adapted to receive data representative of the condition and/or infection status of the device wearer from one or more of the sensors and/or determine the onset or presence of an infection based upon the data received from the sensor(s). As used herein, the term "data" can include a single datum or a plurality of data values or statistics. The term "statistics" can include any appropriate mathematical calculation or metric relative to data interpretation, e.g., probability, confidence interval, distribution, range, or the like. Further, as used herein, the term "monitoring time period" means a period of time over which characteristics of the subject are measured and statistics are determined. The monitoring time period can be any suitable length of time, e.g., 1 millisecond, 1 second, 10 seconds, 30 seconds, 1 minute, 10 minutes, 30 minutes, 1 hour, etc., or a range of time between any of the foregoing time periods.

Any suitable technique or techniques can be utilized to determine statistics for the various data from the sensors, e.g., direct statistical analyses of time series data from the sensors, differential statistics, comparisons to baseline or statistical models of similar data, etc. Such techniques can be general or individual-specific and represent long-term or short-term behavior. These techniques could include standard pattern classification methods such as Gaussian mixture models, clustering as well as Bayesian approaches, machine learning approaches such as neural network models and deep learning, and the like.

Further, in some embodiments, the controller can be adapted to compare data, data features, and/or statistics against various other patterns, which could be prerecorded data patterns (baseline patterns) of the particular individual wearing an ear-wearable device herein, prerecorded data patterns (group baseline patterns) of a group of individuals wearing ear-wearable devices herein, one or more predetermined data patterns that serve as patterns indicative of an occurrence of an infection (positive example patterns), one or more predetermined data patterns that serve as patterns indicative of the absence of an infection (negative example patterns), or the like. As merely one scenario, if a data pattern is detected in an individual that exhibits similarity crossing a threshold value to a particular positive example pattern or substantial similarity to that pattern, wherein the pattern is specific for an infection, then that can be taken as an indication of an occurrence of an infection.

Similarity and dissimilarity can be measured directly via standard statistical metrics such normalized Z-score, or similar multidimensional distance measures (e.g., Mahalanobis or Bhattacharyya distance metrics), or through similarities of modeled data and machine learning. These techniques can include standard pattern classification methods such as Gaussian mixture models, clustering as well as Bayesian approaches, neural network models, and deep learning.

As used herein the term "substantially similar" means that, upon comparison, the sensor data are congruent or have statistics fitting the same statistical model, each with an acceptable degree of confidence. The threshold for the acceptability of a confidence statistic may vary depending upon the subject, sensor, sensor arrangement, type of data, context, condition, etc.

The statistics associated with an infection of an individual over the monitoring time period can be determined by utilizing any suitable technique or techniques, e.g., standard pattern classification methods such as Gaussian mixture models, clustering, hidden Markov models, as well as Bayesian approaches, neural network models, and deep learning.

Various embodiments herein specifically include the application of a machine learning classification model. In various embodiments, the ear-wearable devices and/or systems herein can be configured to periodically update the machine learning classification model based on known occurrences of infection of the device wearer.

In some embodiments, a training set of data can be used in order to generate a machine learning classification model. The input data can include microphone and/or sensor data as described herein as tagged/labeled with binary and/or non-binary classifications of infection. Binary classification approaches can utilize techniques including, but not limited to, logistic regression, k-nearest neighbors, decision trees, support vector machine approaches, naive Bayes techniques, and the like. Multi-class classification approaches (e.g., for non-binary classifications of infection) can include k-nearest neighbors, decision trees, naive Bayes approaches, random forest approaches, and gradient boosting approaches amongst others.

In some embodiments, to facilitate a supervised machine learning approach, a device wearer can be put through a particular movement protocol (such as a particular walking protocol) in order to provide a training set of data that is specific for the device wearer. In some embodiments, a training set of data specific for the device wearer can be gathered as part of a fitting procedure associated with the device wearer getting the device(s). However, in other embodiments, unsupervised machine learning approaches can also be used.

In various embodiments, the device and/or system herein is configured to execute operations to generate or update the machine learning model on the ear-wearable device itself. In some embodiments, the ear-wearable device may convey data to another device such as an accessory device or a cloud computing resource in order to execute operations to generate or update a machine learning model herein.

Sensor Package

Various embodiments herein include a sensor package. The sensor package can include one or more sensors. As such, devices and systems herein can include one or more sensors (including one or more discrete or integrated sensors) to provide data for use with operations to evaluate and/or characterize the infection status of a device wearer. Further details about the sensors are provided as follows. However, it will be appreciated that this is merely provided by way of example and that further variations are contemplated herein. Also, it will be appreciated that a single sensor may provide more than one type of physiological data. For example, heart rate, respiration, blood pressure, or any combination thereof may be extracted from PPG (photoplethysmography) sensor data.

Sensors herein can include motion sensors, a microphone, a heart rate sensor, a heart rate variability sensor, an electrocardiogram (ECG) sensor, a blood oxygen sensor, a blood pressure sensor, a skin conductance sensor, a photoplethysmography (PPG) sensor, a temperature sensor (such as a core body temperature sensor, skin temperature sensor, ear-canal temperature sensor, or another temperature sensor), a motion sensor, an electroencephalograph (EEG) sensor, and a respiratory sensor, amongst others. In various embodiments, the motion sensor can include at least one of an accelerometer and a gyroscope.

Devices herein can specifically include one or more motion sensors (or movement sensors) amongst other types of sensors. Motion sensors herein can include inertial measurement units (IMU), accelerometers, gyroscopes, barometers, altimeters, and the like. The IMU can be of a type disclosed in commonly owned U.S. patent application Ser. No. 15/331,230, filed Oct. 21, 2016, which is incorporated herein by reference. In some embodiments, electromagnetic communication radios or electromagnetic field sensors (e.g., telecoil, NFMI, TMR, GMR, etc.) sensors may be used to detect motion or changes in position. In some embodiments, biometric sensors may be used to detect body motions or physical activity. Motion sensors can be used to track movements of a patient in accordance with various embodiments herein.

In some embodiments, the motion sensors can be disposed in a fixed position with respect to the head of a patient, such as worn on or near the head or ears. In some embodiments, operatively connected motion sensors can be worn on or near another part of the body such as on a wrist, arm, or leg of the patient.

According to various embodiments, sensors herein can include one or more of an IMU, and accelerometer (3, 6, or 9 axis), a gyroscope, a barometer, an altimeter, a magnetometer, a magnetic sensor, an eye movement sensor, a pressure sensor, an acoustic sensor, a telecoil, a heart rate sensor, a global positioning system (GPS) circuit, a temperature sensor, a blood pressure sensor, an oxygen saturation sensor, an optical sensor, a blood glucose sensor (optical or otherwise), a galvanic skin response sensor, a cortisol level sensor (optical or otherwise), a microphone, acoustic sensor, an electrocardiogram (ECG) sensor, electroencephalography (EEG) sensor which can be a neurological sensor, eye movement sensor (e.g., electrooculogram (EOG) sensor), myographic potential electrode sensor (or electromyography—EMG), a heart rate monitor, a pulse oximeter or oxygen saturation sensor (SpO2), a wireless radio antenna, blood perfusion sensor, hydrometer, sweat sensor, cerumen sensor, air quality sensor, pupillometry sensor, cortisol level sensor, hematocrit sensor, light sensor, image sensor, and the like.

In some embodiments, sensors herein can be part of an ear-wearable device. However, in some embodiments, the sensors utilized can include one or more additional sensors that are external to an ear-wearable device. For example, various of the sensors described above can be part of a wrist-worn or ankle-worn sensor package, or a sensor package supported by a chest strap. In some embodiments, sensors herein can be disposable sensors that are adhered to the device wearer ("adhesive sensors") and that provide data to the ear-wearable device or another component of the system.

Data produced by the sensor(s) herein can be operated on by a processor of the device or system.

As used herein the term "inertial measurement unit" or "IMU" shall refer to an electronic device that can generate signals related to a body's specific force and/or angular rate. IMUs herein can include one or more accelerometers (3, 6, or 9 axis) to detect linear acceleration and a gyroscope to detect rotational rate. In some embodiments, an IMU can also include a magnetometer to detect a magnetic field.

As used herein, the term "microphone" shall include reference to all types of devices used to capture sounds including various types of microphones (including, but not limited to, carbon microphones, fiber optic microphones, dynamic microphones, electret microphones, ribbon microphones, laser microphones, condenser microphones, cardioid microphones, crystal microphones) and vibration sensors (including, but not limited to accelerometers and various types of pressure sensors). Microphones herein can include analog and digital microphones. Systems herein can also include various signal processing chips and components such as analog-to-digital converters and digital-to-analog converters. Systems herein can operate with audio data that is gathered, transmitted, and/or processed reflecting various sampling rates. By way of example, sampling rates used herein can include 8,000 Hz, 11,025 Hz, 16,000 Hz, 22,050 Hz, 32,000 Hz, 37,800 Hz, 44,056 Hz, 44,100 Hz, 47,250 Hz, 48,000 Hz, 50,000 Hz, 50,400 Hz, 64,000 Hz, 88,200 Hz, 96,000 Hz, 176,400 Hz, 192,000 Hz, or higher or lower, or within a range falling between any of the foregoing. Audio data herein can reflect various bit depths including, but not limited to 8, 16, and 24-bit depth. Microphones herein can include both directional and omnidirectional microphones. In some embodiments, microphones herein can be configured to be sensitive to sounds coming from the direction of the device wearer's feet to more sensitively pick up the sound of foot falls while walking. In some embodiments, microphones herein can include inward facing microphones to be more sensitive to pickup foot fall sounds through the body.

An eye movement sensor herein may be, for example, an electrooculographic (EOG) sensor, such as an EOG sensor disclosed in commonly owned U.S. Pat. No. 9,167,356, which is incorporated herein by reference. A pressure sensor herein can be, for example, a MEMS-based pressure sensor, a piezo-resistive pressure sensor, a flexion sensor, a strain sensor, a diaphragm-type sensor and the like.

A temperature sensor herein can be, for example, a thermistor (thermally sensitive resistor), a resistance temperature detector, a thermocouple, a semiconductor-based sensor, an infrared sensor, or the like.

A blood pressure sensor herein can be, for example, a pressure sensor. In various embodiments, a pressure sensor herein can include at least one of a piezoelectric sensor and a graphene sensor. In some embodiments, a blood pressure sensor can be part of a PPG sensor wherein blood pressure is derived based on analysis of the PPG sensor waveform. The heart rate sensor can be, for example, an electrical signal sensor, an acoustic sensor, a pressure sensor, an infrared sensor, an optical sensor, or the like.

An oxygen saturation sensor (such as a blood oximetry sensor) herein can be, for example, an optical sensor, an infrared sensor, a visible light sensor, or the like.

An electrical signal sensor herein can include two or more electrodes and can include circuitry to sense and record electrical signals including sensed electrical potentials and the magnitude thereof (according to Ohm's law where V=IR) as well as measure impedance from an applied electrical potential.

It will be appreciated that sensors herein can include one or more sensors that are external to the ear-wearable device. In addition to the external sensors discussed hereinabove, the sensor package can comprise a network of body sensors (such as those listed above) that sense movement of a multiplicity of body parts (e.g., arms, legs, torso). In some embodiments, the ear-wearable device can be in electronic communication with the sensors or processor of a medical device.

In various embodiments, the sensor package can include an optical color sensor.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. An ear-wearable infection sensor device comprising:
- a control circuit;
- a microphone, wherein the microphone is in electrical communication with the control circuit;
- a sensor package, wherein the sensor package is in electrical communication with the control circuit; and
- an electroacoustic transducer, wherein the electroacoustic transducer is in electrical communication with the control circuit;
- wherein the ear-wearable infection sensor device is configured to;
  - analyze data from the sensor package to determine physiological parameters of a device wearer, the physiological parameters comprising a temperature;
  - evaluate a duration of a temperature elevation; and
  - evaluate the physiological parameters to detect a risk of an infection.

2. The ear-wearable infection sensor device of claim 1, the physiological parameters comprising at least one of a respiration rate, a heart rate, and SpO2.

3. The ear-wearable infection sensor device of claim 1, the sensor package comprising a temperature sensor, wherein the temperature sensor is configured for placement within the ear canal.

4. The ear-wearable infection sensor device of claim 1, the sensor package comprising:
- a pressure sensor; and
- a motion sensor;
- wherein the ear-wearable infection sensor device is configured to detect orthostatic hypotension using data from the pressure sensor and the motion sensor.

5. The ear-wearable infection sensor device of claim 1, wherein the ear-wearable infection sensor device is configured to compare the physiological parameters reflecting the device wearer in a resting state versus the device wearer in a non-resting state.

6. The ear-wearable infection sensor device of claim 1, wherein the ear-wearable infection sensor device is configured to evaluate breathing sounds.

7. The ear-wearable infection sensor device of claim 6, wherein the ear-wearable infection sensor device is configured to evaluate left-side versus right-side breathing sounds.

8. The ear-wearable infection sensor device of claim 6, wherein the ear-wearable infection sensor device is configured to identify a cough.

9. The ear-wearable infection sensor device of claim 8, wherein the ear-wearable infection sensor device is configured to distinguish between a wet cough and a dry cough.

10. The ear-wearable infection sensor device of claim 1, wherein the ear-wearable infection sensor device is configured to generate a sound and record received reflected sound.

11. The ear-wearable infection sensor device of claim 1, the sensor package comprising an optical color sensor, wherein the ear-wearable infection sensor device is configured to evaluate a real-time skin color compared with a baseline skin color for the device wearer.

12. The ear-wearable infection sensor device of claim 1, wherein the ear-wearable infection sensor device is configured to classify a set of data from at least one of the sensor package and the microphone into a category from amongst a set of categories.

13. The ear-wearable infection sensor device of claim 12, wherein the category reflects a probability of an infection.

14. The ear-wearable infection sensor device of claim 1, wherein the ear-wearable infection sensor device is configured to instruct the device wearer to look at an accessory device with a camera if a risk of infection is detected.

15. The ear-wearable infection sensor device of claim 1, wherein the ear-wearable infection sensor device is configured to change a threshold for detecting the risk of an infection based on data regarding previous infections experienced by the device wearer.

16. The ear-wearable infection sensor device of claim 1, wherein the ear-wearable infection sensor device is configured to change a threshold for detecting the risk of an infection based on data regarding previous surgical procedures experienced by the device wearer.

17. An ear-wearable infection sensor system comprising:

a first ear-wearable device, the first ear-wearable device comprising:

a first control circuit;

a first microphone, wherein a microphone is in electrical communication with a control circuit;

a first electroacoustic transducer, wherein an electroacoustic transducer is in electrical communication with the control circuit; and a first sensor package, wherein a sensor package is in electrical communication with the control circuit;

a second ear-wearable device, the second ear-wearable device comprising:

a second control circuit;

a second microphone, wherein the second microphone is in electrical communication with the second control circuit;

a second electroacoustic transducer, wherein the second electroacoustic transducer is in electrical communication with the second control circuit; and a second sensor package, wherein the second sensor package is in electrical communication with the second control circuit;

wherein the ear-wearable infection sensor system is configured to:

analyze data from the first and/or second sensor package to determine physiological parameters of a device wearer; and evaluate the physiological parameters along with data regarding an activity level of the device wearer to detect a risk of an infection.

18. The ear-wearable infection sensor system of claim 17, wherein the ear-wearable infection sensor system is configured to:

detect a level of physical activity of the device wearer;

if the detected level physical activity is at or below a threshold level, enter an active operation mode wherein the system detects the risk of infection;

if the detected level physical activity is above a threshold level, enter a suspended operation mode wherein the system does not detect the risk of infection.

19. The ear-wearable infection sensor device of claim 1, wherein the ear-wearable infection sensor device is configured to:

evaluate circadian variations in temperature of the device wearer;

determine a circadian corrected baseline temperature of the device wearer;

detect the risk of infection by comparing an instantaneous temperature of the device wearer to the circadian corrected baseline temperature of the device wearer.

20. The ear-wearable infection sensor device of claim 1, further comprising a geolocation circuit configured to assess location-specific infection risks.

* * * * *